United States Patent
Shahmoon et al.

(10) Patent No.: US 11,640,027 B2
(45) Date of Patent: May 2, 2023

(54) ENHANCING IMAGING BY MULTICORE FIBER ENDOSCOPES

(71) Applicant: ZSQUARE LTD., Petah Tikva (IL)

(72) Inventors: Asaf Shahmoon, Petah Tikva (IL); Zeev Zalevsky, Rosh Ha'ayin (IL)

(73) Assignee: ZSQUARE LTD., Petah Tikva (IL)

( * ) Notice: Subject to any disclaimer, the term of this patent is extended or adjusted under 35 U.S.C. 154(b) by 0 days.

(21) Appl. No.: 17/372,471

(22) Filed: Jul. 11, 2021

(65) Prior Publication Data

US 2021/0341670 A1 Nov. 4, 2021

Related U.S. Application Data

(63) Continuation of application No. 16/631,750, filed as application No. PCT/IL2018/050779 on Jul. 16, 2018, now Pat. No. 11,061,185.

(Continued)

(51) Int. Cl.
  *G02B 6/02* (2006.01)
  *A61B 1/00* (2006.01)
  *G02B 6/42* (2006.01)

(52) U.S. Cl.
  CPC ........ *G02B 6/02042* (2013.01); *A61B 1/0017* (2013.01); *A61B 1/00167* (2013.01);
  (Continued)

(58) Field of Classification Search
  None
  See application file for complete search history.

(56) References Cited

U.S. PATENT DOCUMENTS

| 5,295,018 A | 3/1994 | Konuma et al. |
| 5,716,122 A | 2/1998 | Esaki et al. |

(Continued)

FOREIGN PATENT DOCUMENTS

| EP | 2156785 | 2/2010 |
| EP | 2374427 | 10/2011 |
| WO | WO2010/143402 | 12/2010 |

OTHER PUBLICATIONS

Extended European Search Report for European Application No. 18836075.4 dated Mar. 18, 2021.

(Continued)

*Primary Examiner* — Jerry Rahll
(74) *Attorney, Agent, or Firm* — Pearl Cohen Zedek Latzer Baratz LLP

(57) ABSTRACT

Multicore fibers and endoscope configurations are provided, along with corresponding production and usage methods. Various configurations include an adiabatically tapered proximal fiber tip and/or proximal optical elements for improving the interface between the multicore fiber and the sensor, photonic crystal fiber configurations which reduce the attenuation along the fiber, image processing methods and jointed rigid links configurations for the endoscope which reduce attenuation while maintaining required flexibility and optical fidelity. Various configurations include spectral multiplexing approaches, which increase the information content of the radiation delivered through the fibers and endoscope, and configurations which improve image quality, enhance the field of view, provide longitudinal information. Various configurations include fiber-based wave-front sensors. Many of the disclosed configurations increase the imaging resolution and enable integration of additional modes of operation while maintain the endoscope (Continued)

very thin, such as spectral imaging and three dimensional imaging.

9 Claims, 12 Drawing Sheets

Related U.S. Application Data

(60) Provisional application No. 62/533,155, filed on Jul. 17, 2017.

(52) U.S. Cl.
CPC ........ *G02B 6/4204* (2013.01); *A61B 1/00197* (2013.01); *G02B 6/02328* (2013.01); *G02B 6/4202* (2013.01)

(56) References Cited

U.S. PATENT DOCUMENTS

| 2011/0268141 | A1  |        | 11/2011 | Nakatate       |            |
|--------------|-----|--------|---------|----------------|------------|
| 2011/0280517 | A1  |        | 11/2011 | Fini et al.    |            |
| 2016/0022119 | A1  | *      | 1/2016  | Shahmoon       | A61B 1/00174 |
|              |     |        |         |                | 600/182    |
| 2017/0100024 | A1  |        | 4/2017  | Shahmoon et al.|            |
| 2017/0146371 | A1  |        | 5/2017  | Kozlov et al.  |            |
| 2017/0245735 | A1  |        | 8/2017  | Wang           |            |
| 2020/0187766 | A1  |        | 6/2020  | Zalevsky et al.|            |

OTHER PUBLICATIONS

H. Dammann and E. Klotz, "Coherent Optical Generation and Inspection of Two-dimensional Periodic Structures," Optica Acta: International Journal of Optics 24(4), 505-515 (1977).

R. V. Shack and B. C. Platt, "Production and use of a lenticular Hartmann screen," paper presented at the 1971 Spring Meeting of the Optical Society of America, abstract printed on p. 656 of the Program of the 1971 Spring Meeting of the Optical Society of America, Journal of the Optical Society of America, vol. 61, pp. 648-697 (1971).

Office Action for JP Application No. 2020-501791 dated Aug. 2, 2022.

International Search Report for PCT Application No. PCT/IL2018/050779 dated Nov. 8, 2018.

* cited by examiner

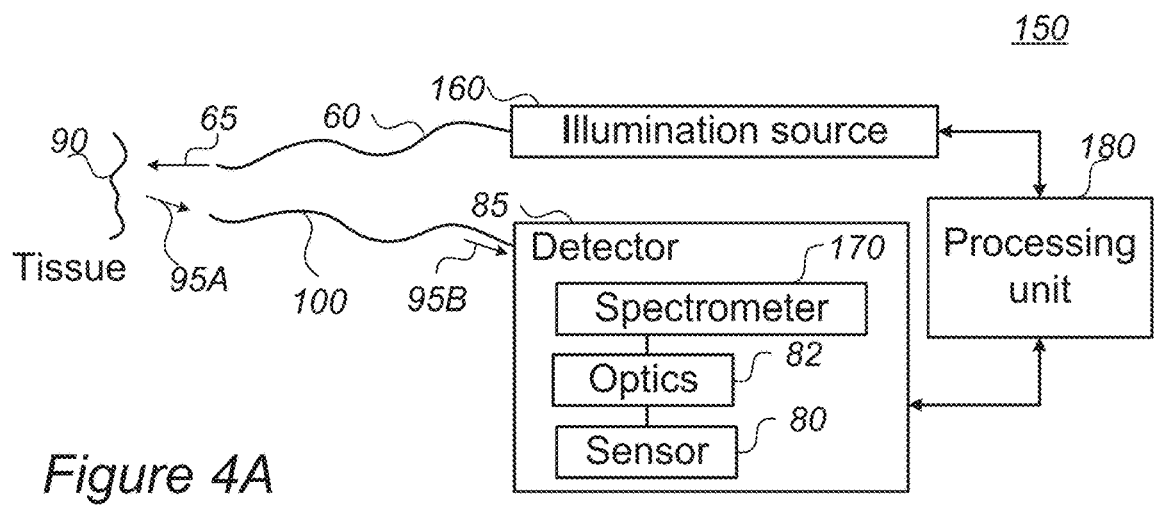
Figure 4A
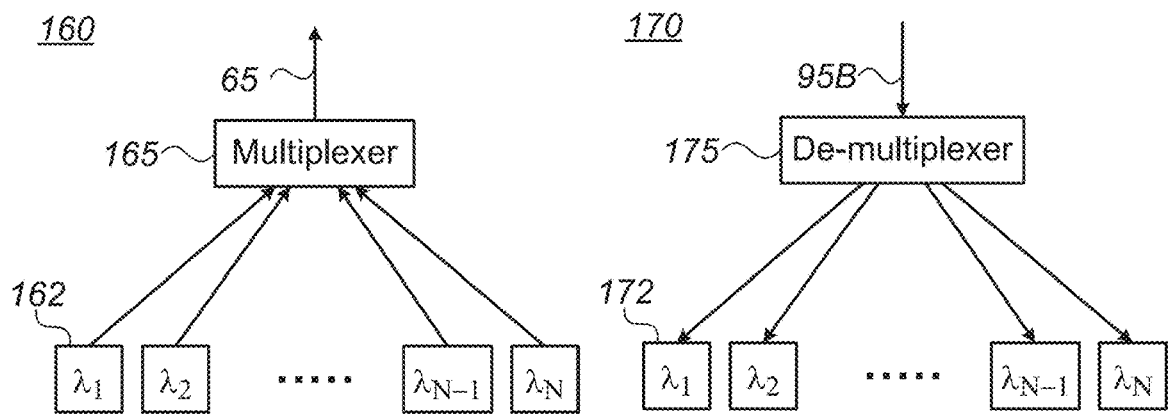
Figure 4B
Figure 4C
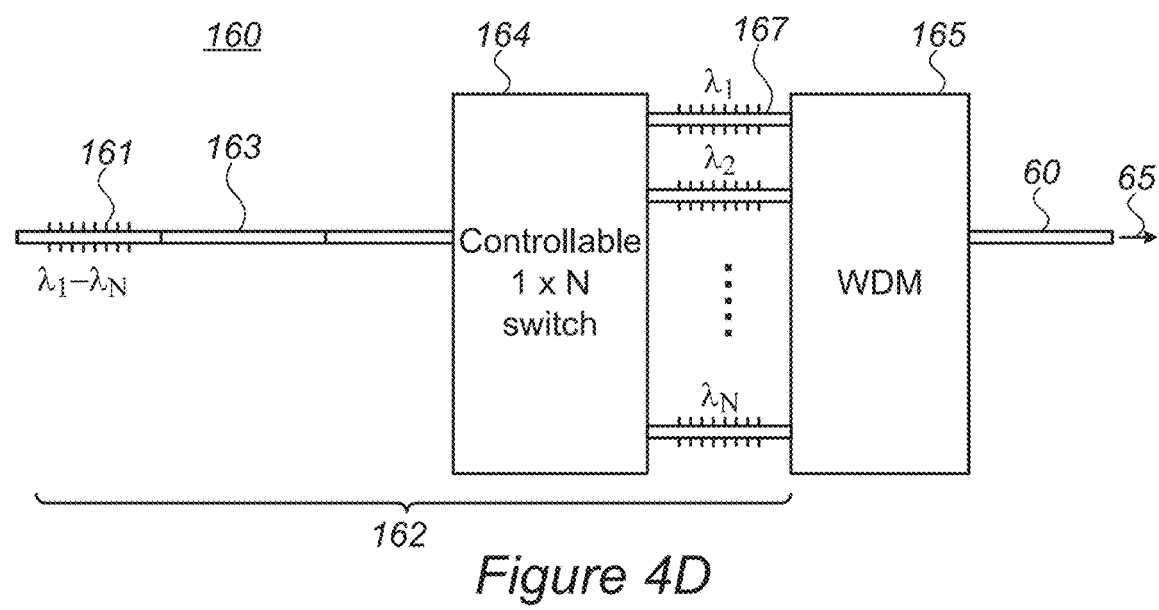
Figure 4D

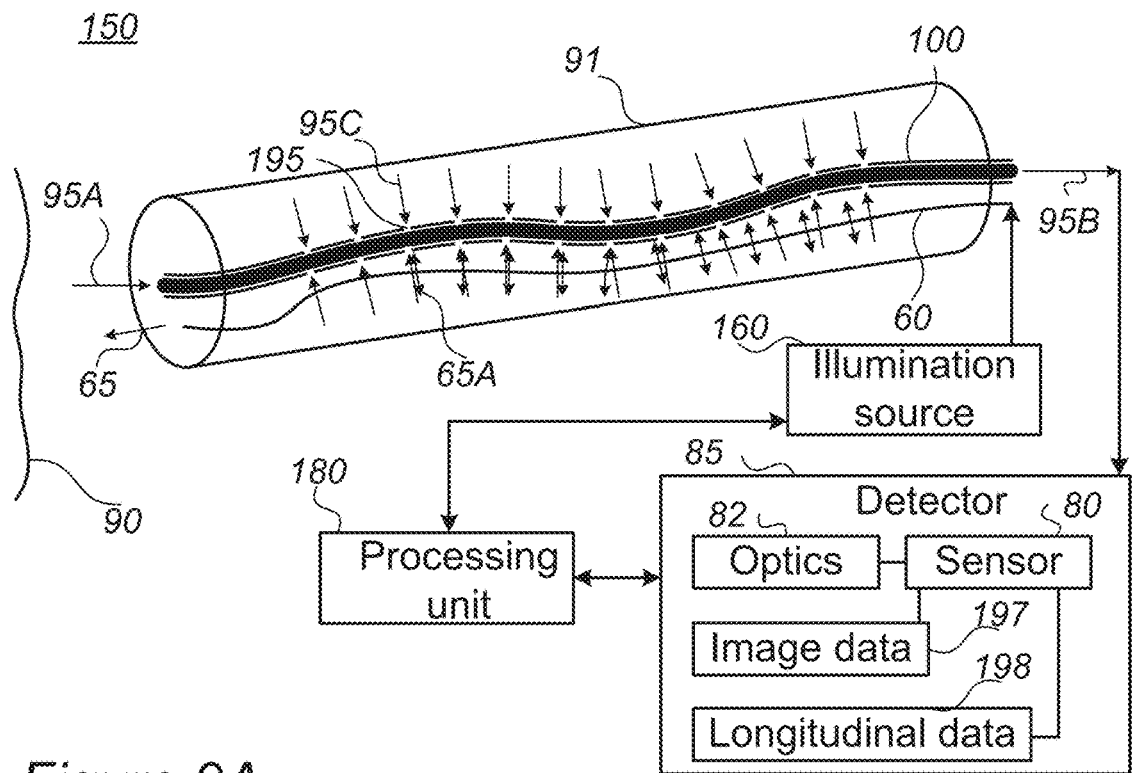
Figure 9A
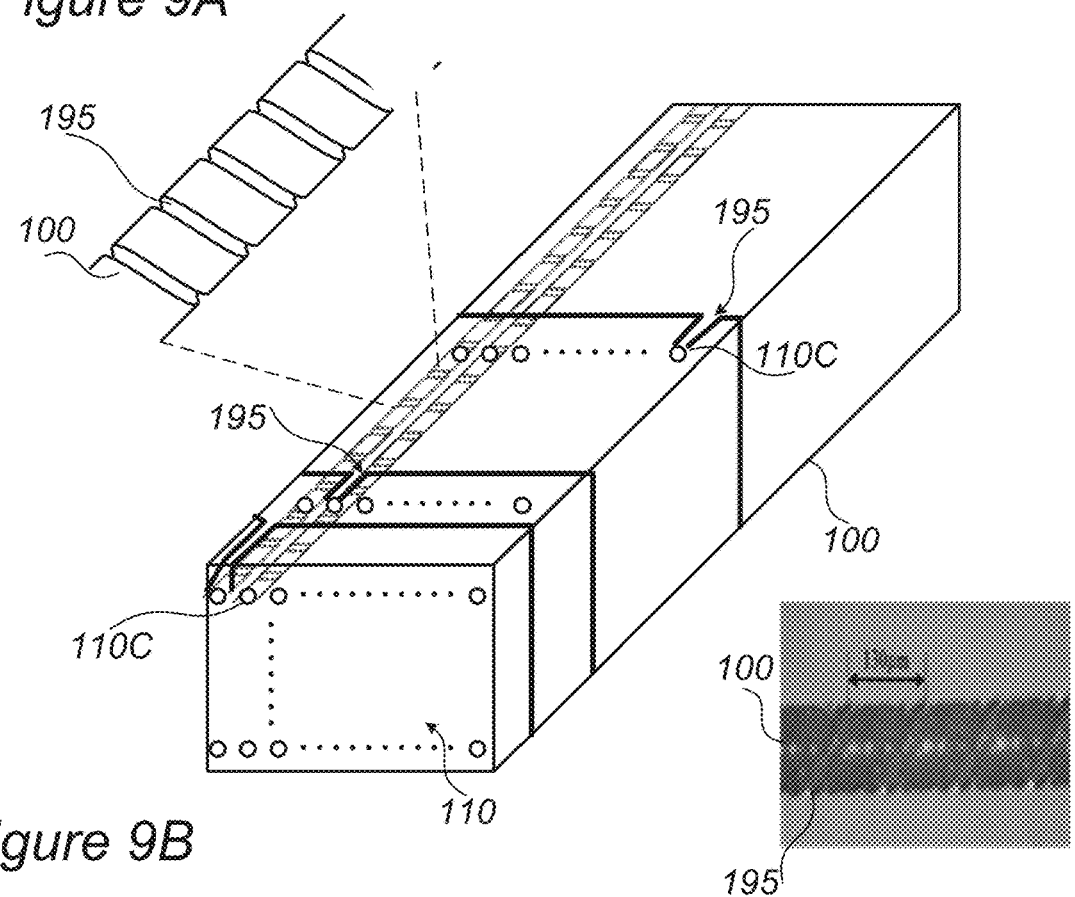
Figure 9B
Figure 9C

ENHANCING IMAGING BY MULTICORE FIBER ENDOSCOPES

CROSS-REFERENCE TO RELATED APPLICATIONS

This application is a continuation of U.S. patent application Ser. No. 16/631,750, filed Jan. 16, 2020 as a U.S. National Phase Application of PCT International Application No. PCT/IL2018/050779, International Filing Date Jul. 16, 2018, claiming the benefit of and priority to U.S. Provisional Patent Application No. 62/533,155, filed Jul. 17, 2017, each of which is hereby incorporated by reference in its entirety.

BACKGROUND OF THE INVENTION

1. Technical Field

The present invention relates to the field of endoscopy, and more particularly, to multicore fiber endoscopes.

2. Discussion of Related Art

Endoscopes in various configurations allow efficient treatment of a range of medical problems, as well as means for manipulating different situations with limited access. Endoscope operations are challenging in that illumination, detection and treatment are confined to long and narrow operations modes. Fiber optics technology is a central enabler for such techniques, and fiber-based endoscope experience continuous improvements.

SUMMARY OF THE INVENTION

The following is a simplified summary providing an initial understanding of the invention. The summary does not necessarily identify key elements nor limit the scope of the invention, but merely serves as an introduction to the following description.

Various aspects of the present invention provide multicore fibers and endoscope configurations, along with corresponding production and usage methods, which any of adiabatically tapered proximal fiber tips and/or proximal optical elements, for improving the interface between the multicore fiber and the sensor, photonic crystal fiber configurations which reduce the attenuation along the fiber, jointed rigid links configurations which reduce attenuation while maintaining required flexibility and optical fidelity, image processing methods, spectral multiplexing approaches, which increase the information content of the radiation delivered through the fibers and endoscope, as well as fiber-based wave-front sensors.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 4A-4D are high level schematic illustrations of an endoscope and illumination sources thereof, according to some embodiments of the invention.

FIGS. 9A-9C are high level schematic illustrations of longitudinally-sensing endoscopes, according to some embodiments of the invention.

DETAILED DESCRIPTION OF THE INVENTION

Figure 1A:
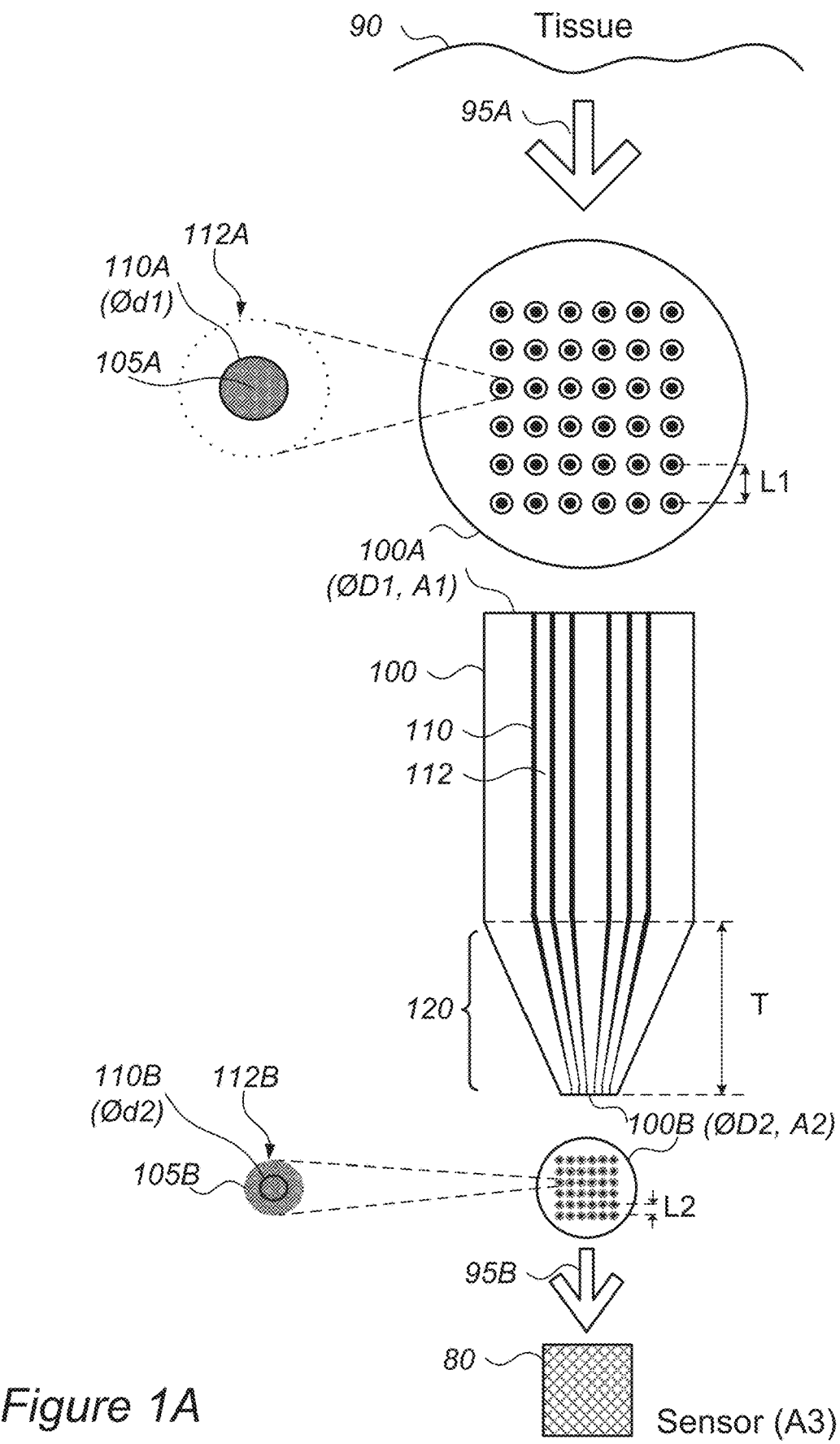
FIG. 1A is a high level schematic illustration of a multicore imaging fiber having a proximal tapered end, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing". "computing", "calculating", "determining", "enhancing", "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units may be at least partially implemented by a computer processor.

Multicore fibers and endoscope configurations are provided, along with corresponding production and usage methods. Various configurations include an adiabatically tapered proximal fiber tip and/or proximal optical elements for improving the interface between the multicore fiber and the sensor, photonic crystal fiber configurations which reduce the attenuation along the fiber, image processing methods and jointed rigid links configurations for the endoscope which reduce attenuation while maintaining required flexibility and optical fidelity. Various configurations include spectral multiplexing approaches, which increase the information content of the radiation delivered through the fibers and endoscope, and configurations which improve image quality, enhance the field of view, provide longitudinal information. Various configurations include fiber-based wave-front sensors. Many of the disclosed configurations increase the imaging resolution and enable integration of additional modes of operation while maintain the endoscope very thin, such as spectral imaging and three dimensional imaging. It is noted that while the following refers to tissue as the imaging object, any other element, object, surface or part may be imaged by the disclosed fibers and endoscopes, and the term "tissue" is not to be taken as limiting the invention in any way. It is further noted that configurations are disclosed separately to merely to simplify the respective explanations, and configurations may be combined to for endoscopes with two or more of the configurations which may be illustrated in different figures and/or disclosed in different embodiments, Tapered End FIG. 1A is a high level schematic illustration of a multi-core imaging fiber 100 having a proximal tapered end 120, according to some embodiments of the invention. Multicore imaging fiber 100 receives radiation 95A from imaged tissue 90 (as a non-limiting example) at a distal end 100A of fiber 100, transmits the radiation throughout the fiber's length and delivers radiation 95B to a sensor 80 at a proximal end 100B of fiber 100. Multicore imaging fiber 100 may comprise a large number of cores 110 within a common cladding and/or multiple cladding structures 112, e.g., multicore imaging fiber 100 may comprise tens or hundreds of thousands cores 110. FIG. 1A illustrates schematically only few cores 110 for explanatory purposes. Certain embodiments comprise endoscopes comprising multicore imaging fiber 100.

For example, multicore imaging fiber 100 may comprise at least 10,000 cores 110 (possibly 50,000 cores, 100,000 cores or any intermediate or other number) with a common cladding 112 and have proximal tip 100A configured to deliver image radiation 95A from tissue 90 at distal end 100B of fiber 100. Image radiation 105A may be confined to cores 110A (having a diameter d1. e.g., between 0.5-2 µm, between 1-1.5 µm etc.) and cores 110A may be interspaced within fiber cross-sectional area A1 (having a diameter D1, with cores 110A interspaced, L1. e.g., by several µm. e.g., 3-5 µm) to prevent cross-talk between cores 110A. Cross section 100A may be prevalent from distal end 100A and throughout all of fiber 100, but for tapered end 120 thereof, and is illustrated to show each core 110A surrounded by cladding material or structures 112A and with image radiation 105A confined to core 110A. It is noted that cores 110 may have a varying degree of order, and may be dispersed through the fiber cross section with a certain degree of randomness. The interspacing, or pitch L1 between cores 110 may be understood as average or median interspacing.

Proximal tip with tapered end 120 may be very short, e.g., shorter than e.g., 2 cm, 1cm, 0.5 cm etc. as indicated by the length T. and be adiabatically tapered to reduce the fiber cross-sectional area (e.g., from fiber diameter D1 and cross-sectional area A1 to a fiber diameter D2 and cross-sectional area A2) and to reduce the core diameter (e.g., from core diameter d1 of cores 110A to a core diameter d2 of cores 110B, and correspondingly pitch L1 to reduced pitch L2) by a factor of at least 3, allowing image radiation 105B to exit narrowed cores 110B. Proximal tip with tapered end 120 may be further configured to deliver image radiation 105B as radiation 95B to an adjacent sensor 80, with an effective image area to sensor area ratio (A3:A2) which is much larger than the ratio of original fiber cross sectional area to sensor area ratio (A3:A1). For example, effective image area to sensor area ratio (A3:A2) may be at least 1:3, 1:2 or even larger, possibly approaching 1:1. The larger ratio of image area to sensor area enables any of: using smaller sensors 80 (as sensor coverage by the image is more efficient), using large sensors 80 more efficiently (with more pixels sensing image data) and/or using simpler sensors 80 (without gaps between pixels, as interspaces between cores 110A are reduced and radiation 105B may be delivered over most or all of the tapered end's cross sectional area A2). Radiation 105B may exit smaller cores 110B at tapered end 120 to deliver radiation 95B to sensor 80 over an area which is larger than the cumulative area of cores 110B, while avoiding crosstalk due to the shortness of proximal end 100B and due to the fact that tapered end 120 is mechanically fixed and cannot bend.

For example, in certain non-limiting embodiments, an effective area of adjacent sensor 80, which receives image radiation 95B from proximal tip 120, may be at least 50% of the total area (A3) of adjacent sensor 80, possibly even at least 70%, 80% or 90% thereof. In certain embodiments, proximal tip 120 may be is shorter than 0.5 cm and/or stiff. In certain embodiments, reduced fiber cross-sectional area A2 may be smaller than 0.1 mm$^2$, reduced core diameter d2 may be smaller than smaller than the optical wavelength in order to cause light to get out of the core and to travel in the cladding area (e.g., smaller than 0.5 µm-500 nm, smaller than 0.4 µm-400 nm, or other values.), and/or reduced core pitch L2 may be smaller than 2 µm.

Advantageously, disclosed designs improve sensor efficiency using multicore fibers. Applying sensing array 80 to present multicore fibers having their proximal end similar of distal end 100A—requires the imaging camera to have enough pixels to sample cores 110A as well as cladding 112A between cores 110A. Moreover, as the camera samples the space uniformly but cores 110A are not completely ordered, regions between cores 110A require waste of camera hardware, namely the sensors have a number of pixels which is much larger than the number of cores 110A in the fiber. In disclosed embodiments however, not only is cross-sectional area 100B much smaller than cross-sectional area 100A, but the spaces between cores 110B are significantly reduced or even avoided, to deliver radiation 95B over most or all of cross-sectional area 100B adjacent to sensor 80 because due to the tapering the light propagating in the tapered section is not confined any more to the core region but rather leaks out to the cladding area. It is noted that while the spreading of radiation 105B beyond narrowed cores 110B provides more efficient use of sensor 80, it does not result in crosstalk between cores 110B and does not limit the bending of fiber 100, as proximal tapered end 120 is very short (and may further be made stiff to prevent bending). For example, in fiber 100 having 80,000 cores 110, sensors 80 may have only one or few 100,000 pixels to detect all radiation 95B. 95A, while prior art fibers (having proximal cross-section 100A) may require several megapixels to detect all radiation from tissue 90.

Optical Reduction of the Effective Fill Factor

Figure 1B:
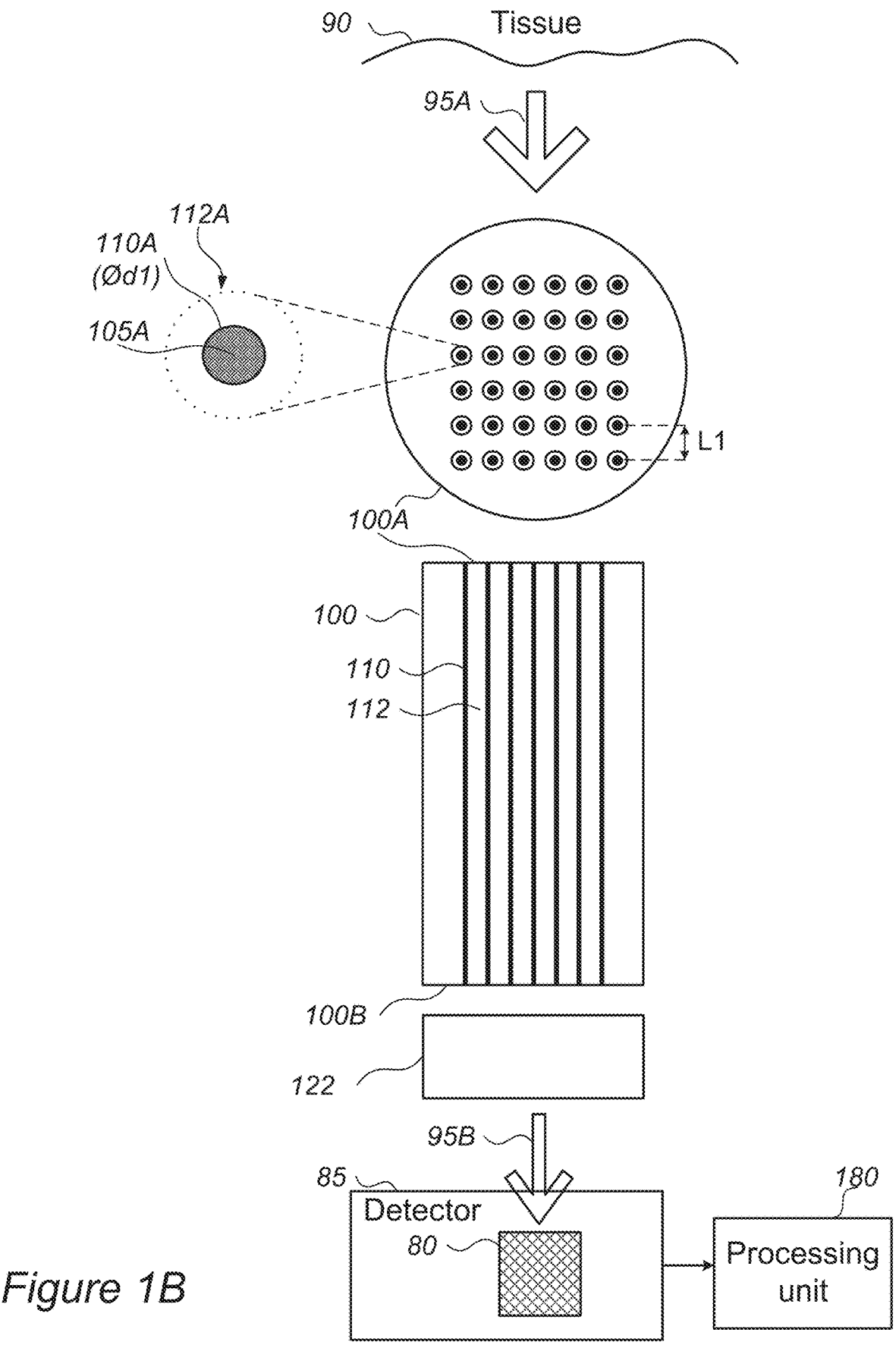
FIG. 1B is a high level schematic illustration of a multicore imaging fiber having a proximal optical element, according to some embodiments of the invention.

FIG. 1B is a high level schematic illustration of a multi-core imaging fiber 100 having a proximal optical element 122, according to some embodiments of the invention. Multicore imaging fiber 100 receives radiation 95A from imaged tissue 90 (as a non-limiting example) at distal end 100A of fiber 100, transmits the radiation throughout the fiber's length and delivers radiation 95B to sensor 80 at proximal end 100B of fiber 100. Multicore imaging fiber 100 may comprise a large number of cores 110 within a common cladding and/or multiple cladding structures 112. e.g., multicore imaging fiber 100 may comprise tens or hundreds of thousands cores 110. Sensor 80 may be part of a detector 85 connected to a processing unit 180 configured to process delivered radiation 95B and form images therefrom.

FIG. 1B illustrates schematically only few cores 110 for explanatory purposes. Certain embodiments comprise endoscopes comprising multicore imaging fiber 100.

For example, multicore imaging fiber 100 may comprise at least 10,000 cores 110 (possibly 50,000 cores, 100,000 cores or any intermediate or other number) with a common cladding 112 and have proximal tip 100A configured to deliver image radiation 95A from tissue 90 at distal end 100B of fiber 100. Image radiation 105A may be confined to cores 110A (having a diameter d1, e.g., between 0.5-2 µm, between 1-1.5 µm etc.) and cores 110A may be interspaced within fiber cross-sectional area A1 (having a diameter D1, with cores 110A interspaced, L1, e.g., by several µm, e.g., 3-5 µm) to prevent cross-talk between cores 110A. Cross section 100A may be prevalent from distal end 100A and throughout all of fiber 100 and is illustrated to show each core 110A surrounded by cladding material or structures 112A and with image radiation 105A confined to core 110A. It is noted that cores 110 may have a varying degree of order, and may be dispersed through the fiber cross section with a certain degree of randomness. The interspacing, or pitch L1 between cores 110 may be understood as average or median interspacing.

Proximal optical element 122 may be set between distal fiber end 100B and sensor 80 and be configured to collect image radiation from cores 110 into a smaller area than the area of distal fiber end 100B, to effectively reduce the fill factor of radiation 95B reaching sensor 80 (the fill factor may be seen as the ration between the image radiation delivering cross sectional area and the total cross sectional area of fiber 100). For example, proximal optical element 122 may comprise one or more prism(s) and/or grating(s) configured to shift closer image radiation from individual cores so that image radiation 95B reaching sensor 80 is at a smaller effective pitch than L. In certain embodiments, delivered radiation 95B may be shifted in a way that mixing the spatial order of cores 110, and detector 85 and/or processing unit 180 may be configured to re-arrange shifted core image radiation to form a correct image. For example, prism(s) with multiple orientations or Dammann grating(s) (see also FIG. 5C for an analogous solution) may be used to implement proximal optical element 122. For example, proximal optical element 122 may be configured to reduce, optically, a fill factor of cores 110 in the fiber cross section by re-orienting the delivered image radiation from cores 110 to fill a smaller area on adjacent sensor 80 with respect to the area of fiber cross section 100B, e.g., to enable using sensor 80 with an area of a third or less of fiber cross section 100B (e.g., the area delimited by cores 110).

It is noted that throughout the disclosure, the term "distal" is used to refer to the ends and associated parts of fiber 100 and/or endoscope 150 which are far from the endoscope's interface (with the detector or the eye of the user) and close to the imaged tissue and to its surroundings, while the term "proximal" is used to refer to the ends and associated parts of fiber 100 and/or endoscope 150 which are close to the endoscope's interface (with the detector or the eye of the user) and far from the imaged tissue and to its surroundings. Concerning cores 110, it is noted that cores 110 may support a single radiation mode, or in certain embodiments, cores may be multimodal, and support more than one radiation mode, as determined by the numerical aperture (NA) and diameter of cores 110 and the delivered wavelength.

It is further noted that fiber 100 and/or endoscope 150 in any of the disclosed embodiments may be used for near or far filed imaging, or any imaging position therebetween. Near field imaging refers to the formation of an image (of imaged objects, tissues and/or their surroundings) at the distal end of the endoscope fiber, typically at the fiber's tip. The image is then typically transferred through the fiber to the detector, possibly through proximal optical elements. Far field imaging refers to the formation of a Fourier transform of imaged objects, tissues and/or their surroundings at the distal end of the endoscope fiber (e.g., the distal end of the endoscope fiber may be at the aperture or pupil plane of the endoscope's optical system), typically at the fiber's tip. The image of the imaged objects, tissues and/or their surroundings may be formed at the proximal end of the endoscope fiber, typically at the fiber's proximal tip or directly on the detector, possibly through proximal optical elements. Near and/or far field imaging may be implemented by various embodiments of optical systems, e.g., direct imaging without any optical elements between the imaged object or tissue and the fiber tip or imaging through any optical element(s) (e.g., lenses). Optical elements may be positioned between the imaged object or tissue and the distal fiber tip, with the distal fiber tip being at least approximately at the Fourier plane (for far field imaging, also termed aperture plane and pupil plane in different contexts) or at the focus plane (for near field imaging, also termed image plane in different contexts) of the optical elements. Intermediate imaging may also be applicable for fiber(s) 100 and/or endoscope(s) 150, with a processing unit being configured to determine the spatial configuration (e.g., relative positions of the Fourier and/or image planes with respect to the fiber's distal tip) and process the delivered radiation from the tissue respectively.

Improving the Resolution

In certain embodiments, endoscope 150 may be operated to provide far field imaging, with distal tip 100A of fiber 100 being at the Fourier plane of the imaging system (deliver Fourier transform of imaged tissue as the delivered radiation), with the output resolution at detector 85 determined by the number of the pixels in the delivered radiation (rather than by the number of cores 110 as in near field imaging), because the Fourier domain is sparse and a small number of cores is sufficient to transmit the spectral information (especially in cases cores 110 are not periodically ordered and thus the sampling of the Fourier is sparse and not uniform/periodic which is even better for properly representing the information of the object that is to be imaged). In certain embodiments, sparse sampling of the Fourier plane, by setting distal end 100A of fiber 100 at a corresponding position with respect to tissue 90 (far field imaging) may be used to improve the resolution of resulting images. e.g., by implementing compressed sensing algorithms, with respect to near field imaging, by overcoming the difficulty of imaging tissue 90 that corresponds to gaps between cores 110 (see e.g., pitch L1 in FIGS. 1A and 1B).

Photonic Crystal Fibers

Figure 2:
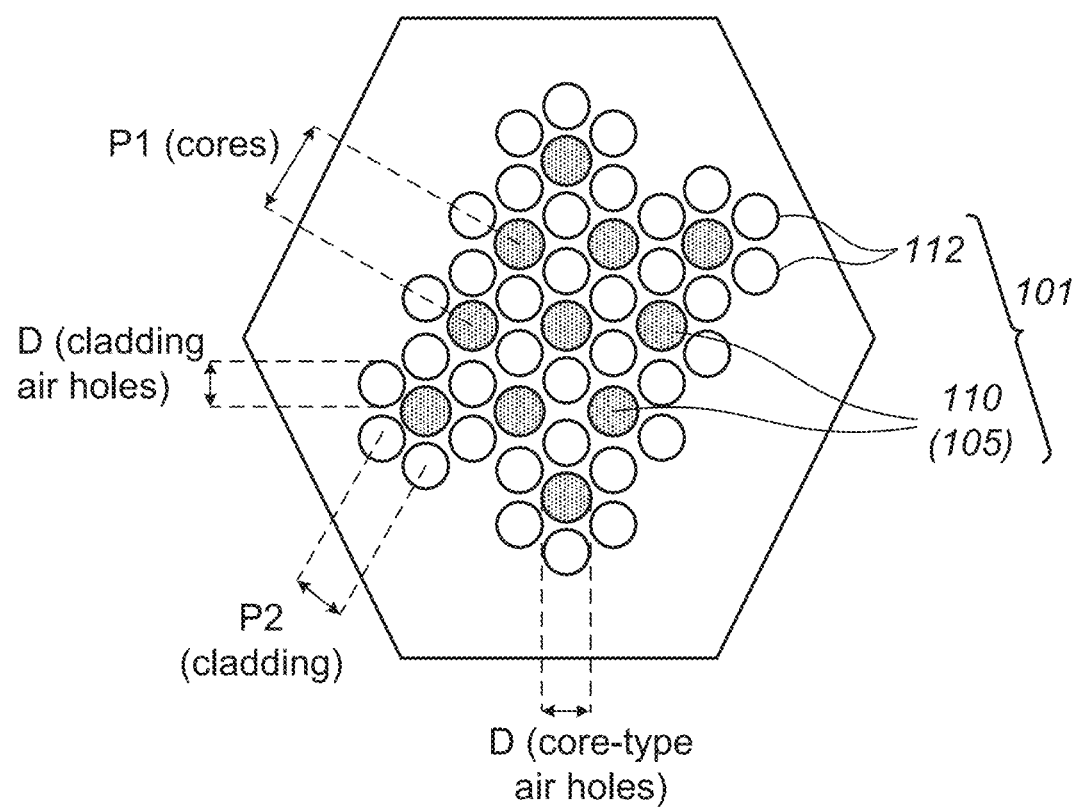
FIG. 2 is a high level schematic illustration of a cross section of a multicore photonic crystal fiber, according to some embodiments of the invention.

FIG. 2 is a high level schematic illustration of a cross section of a multicore photonic crystal fiber 100, according to some embodiments of the invention. Certain embodiments comprise endoscopes comprising multicore imaging fiber 100.

In certain embodiments, multicore fiber 100 may have a photonic crystal structure composed of multiple air holes 101 in at least two types: core-type air holes 110 interspaced within the fiber cross-sectional area at a specified core-pitch P1 selected to confine image radiation 105 within core-type air holes 110, and cladding air-holes 112 (between core-type air holes 110) which are interspaced within the fiber cross-sectional area at a specified cladding-pitch P2 selected to prevent cross-talk between core-type air holes 110. The core diameters (denoted by D's for core-type air holes 110 and cladding air-holes 112) may also be configured to support image radiation confinement within core-type air holes 110 (e.g., the diameter of core-type air holes 110 may be between 0.7-1 µm, e.g., 0.9 µm).

Advantageously, using air holes 101 to provide core-type air holes 110 reduces the attenuation of radiation 105 travelling through cores 110 which are made e.g., of polymer material such as poly(methyl methacrylate) (PMMA), polystyrene (PS) etc. Cladding air-holes 112 are designed to form a periodic structure around each core-type air hole 110 to confine radiation 105 therein due to the spatial periodicity of the cladding structure rather than due to differences in the refraction index as in polymer cores. In effect, multicore fiber 100 may be seen as providing multicore photonic crystal fibers for the first time. For example, in certain embodiments, multicore fiber 100 may have an attenuation coefficient which is smaller by e.g., a factor of 2 per length of 10 cm than a comparable multicore fiber having a same number of polymer cores.

Rigid Links and Joints Structure

Figure 3:
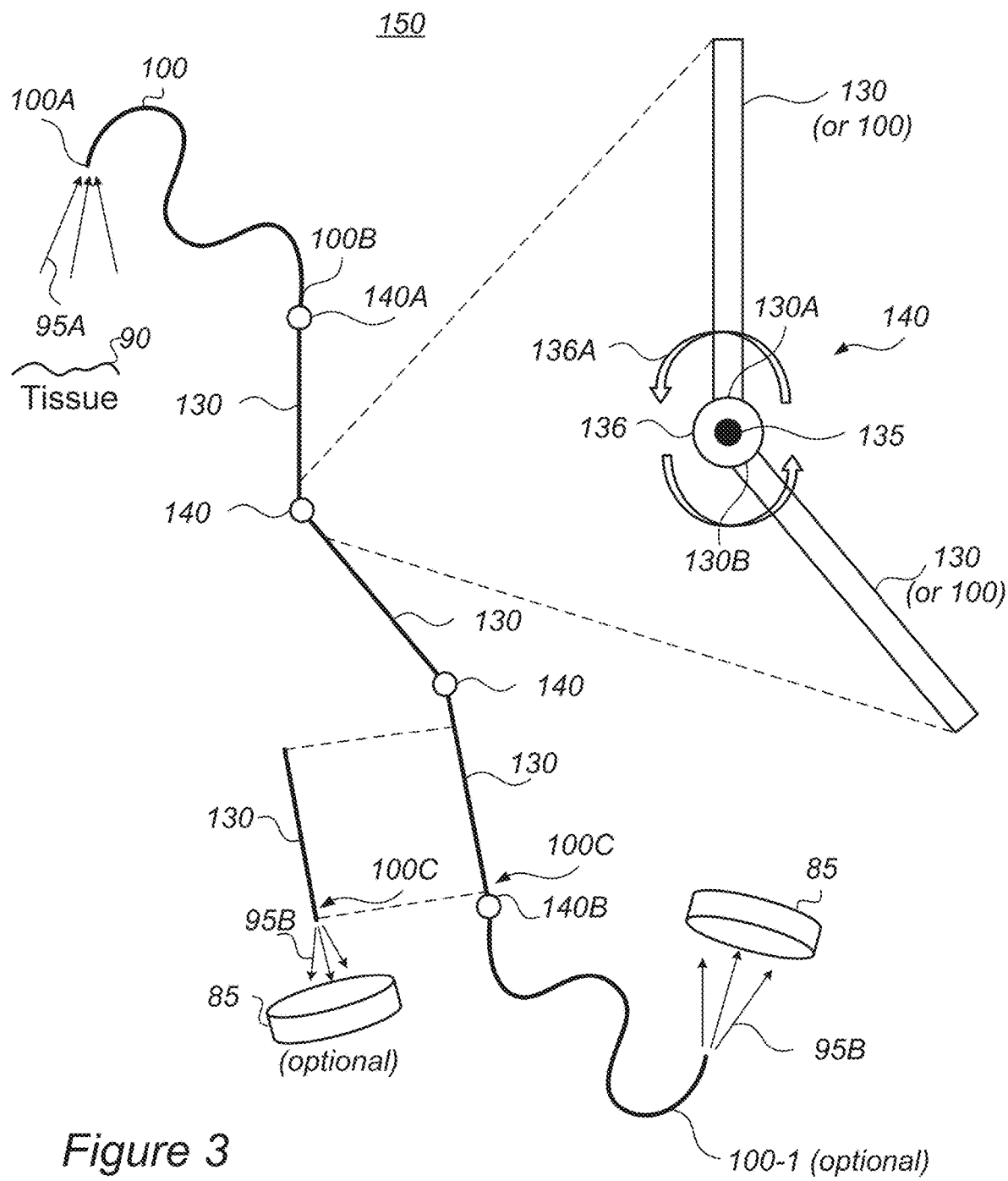
FIG. 3 is a high level schematic illustration of a hybrid endoscope, according to some embodiments of the invention.

FIG. 3 is a high level schematic illustration of a hybrid endoscope 150, according to some embodiments of the invention. Endoscope 150 may comprise distal multicore fiber 100 optically coupled to a plurality of rigid image-relay elements 130, interconnected by a respective plurality of joints 140.

Distal multicore fiber 100, e.g., an imaging fiber, may be configured to receive image radiation 95A from tissue 90 at distal end 100A thereof and deliver the image radiation to proximal end 100B of proximal multicore imaging fiber 100. It is notes that rigid image-relay elements 130 are made of materials which are more transparent in the respective wavelength range than core material of fiber 100, providing overall reduction of attenuation along endoscope 150 (e.g., rigid image-relay elements 130 may be made of glass while fiber cores 110 may be made of polymers which are less transparent). For example, rigid image-relay elements 130 may be GRIN (graded index) rods and/or lenses made of glass.

Rigid image-relay elements 130 interconnected by respective plurality of joints 140, may be configured to deliver radiation travelling through fiber 100 as radiation 95B to a detector 85 (e.g., sensor 80 with corresponding optical element(s)). A distal one of rigid image-relay elements 130 may be connected via a corresponding joint 140A to proximal end 100B of distal multicore imaging fiber 100.

Joints 140A, 140 may be configured to preserve the delivered image radiation from proximal end 100B of distal multicore imaging fiber 100 upon angular movements 136A of rigid image-relay elements 130 with respect to each other, to deliver the image radiation at a proximal end 100C of endoscope 150.

Optionally, endoscope 150 may further comprise a proximal multicore imaging fiber 100-1 connected to a proximal one of rigid image-relay elements 130 via corresponding joint 140B, and configured to deliver the image radiation from proximal rigid image-relay element 130 to detector 85.

Joints 140, 140A. 140B may be designed according to the illustrated design principles, as mechanical-optical joints which preserve the imaging condition between adjacent rigid image-relay elements 130 (as well as thereto and therefrom, relating to joints 140A. 140B to fibers 100, 100-1, respectively) so that light is continuously coupled from one link to the next, at different angles of rotation of rigid image-relay elements 130. It is emphasized that in endoscope 150, imaging is maintained as well as a certain degree of flexibility between rigid elements 130, which may suffice for most of the length of endoscope 150. Multicore fibers 100 may be used only at imaging end 100A of endoscope 150, and possibly at its detector end 100C. Such configurations may be used to yield long endoscopes 150, without limitations resulting from the length of multicore fiber 100 (e.g., attenuation, price, optical performance etc. which at least partly are due to light attenuation through polymer cores 110). Endoscope 150 may further comprise sleeves (not shown) to support the disclosed structure mechanically.

In certain embodiments, at least some, or all of rigid image-relay elements 130 may comprise glass GRIN links and joints 140 may comprise spherical ball lenses 135 positioned within mechanical joints 136 which are connected mechanically to adjacent rigid image-relay elements 130 or fibers 100, 100-1 (for joints 140, 140A. 140B, respectively). Spherical ball lenses 135 may be positioned to preserve, proximad (in proximal direction), the delivered image radiation in any angular relation between adjacent rigid links 130. For example, spherical ball lens 135 may be positioned in the center of mechanical sliding ring 136 in distances fulfilling the imaging condition between an exit face 130A of one link 130 positioned on one side of joint 140 and an entrance face 130B of next adjacent link 130 positioned on the other side of joint 140. Alternatively, optical elements 135 may be used in place of spherical ball lenses 135. Optical elements 135 such as spherical ball lens 135 may be configured to create coupling of light from one link 130 to the next link 130 for any possible angle (or angles within a specified range which is limited mechanically) created between links 130.

Spectral Multiplexing

FIGS. 4A-4D are high level schematic illustrations of endoscope 150 and illumination sources 160 thereof, according to some embodiments of the invention.

Certain embodiments comprise endoscopes 150 comprising an illumination source 160 (see FIG. 4A), configured to deliver illumination 65 (e.g., via one or more illumination fiber(s) 60) at a specified plurality of distinct wavelengths, detector 85 comprising a spectrometer 162 (in addition to sensor 80 and optionally optical elements 82) configured to decode detected radiation 95B in the specified plurality of distinct wavelengths, multicore imaging fiber 100 configured to deliver, through cores 110 to detector 85, image radiation 95A received from tissue 90 illuminated by illumination 65 from illumination source 160, and processing unit 180 configured to derive, from the decoded detected image radiation of each of cores 110, image data corresponding to the specified plurality of distinct wavelengths. Applying illumination at the plurality of distinct wavelengths, simultaneously or sequentially and analyzing received images with respect to the plurality of wavelengths for each core 110, is referred to herein as spectral, or wavelength, multiplexing.

For example, as illustrated schematically in FIG. 4B, multiple input fibers 162 may be configured to deliver the distinct wavelengths (denoted $\lambda_1 \ldots \lambda_N$) as narrowband radiation to a multiplexer 165, e.g., a wavelength-division multiplexer (WDM), which combines the radiation into illumination 65, delivered through illumination fiber 60 to tissue 90. Narrowband input fibers 162 may thus be coupled through multiplexer 165 to deliver multiple distinct wavelengths simultaneously or temporally separated. Correspondingly, as illustrated schematically in FIG. 4C, spectrometer 170 may receive radiation 95B from multicore fiber 100 and separate it into the distinct wavelengths 172 (denoted $\lambda_1 \ldots \lambda_N$), by a de-multiplexer 175, e.g., a wavelength-division multiplexer/de-multiplexer (WDM) (possibly even the same as WDM 165). The resulting narrowband radiation channels 172 may be delivered to sensor(s) 80, e.g., via optics 82, and the resulting data may be delivered to processing unit 180 which may be configured to derive multiple data channels from each core 110. Wavelength multiplexing may thus be configured to increase the information content passed through each core 110 significantly, possibly by factors of tens, hundreds or even thousands, depending on the number of the distinct wavelengths and the ability to crowd narrowband wavelength ranges within the spectrum used for imaging (e.g., in the visible range of ca. 400-700 nm, bandwidths of 3 nm provide N=100 distinct wavelengths denoted $\lambda_1 \ldots \lambda_{100}$).

Disclosed wavelength multiplexing may be used to enhance resolution of endoscope 150 and/or to incorporate additional functionalities or modalities such as OCT (optical coherence tomography), spectroscopical analysis etc. in addition to imaging—to implement multi-functional microendoscope 150. For example, an OCT application may be used to extract depth information for internal tissues 90. In certain embodiments, endoscope 150 may be configured to implement Fourier domain OCT with illumination source 160 being configured to have spectral scanning capability to enable capturing and processing a plurality of 2D images at the range of scanned wavelengths by full field Fourier domain OCT application. In certain embodiments, illumination source 160 may be configured to be spectrally tunable, and images at the plurality of wavelengths may be captured and assembled by processing unit 180 after each (time scanning) of the range of wavelengths, to provide a 2D spatial image with spectral information per each pixel. In certain embodiments, various spectral ranges may be scanned, e.g., fluorescence bands for fluorescent microscopy or other specific ranges—further enhancing the versatility and number of functionalities of endoscope 150.

Multicore imaging fiber 100 and endoscope 150 may be implemented as any of the embodiments disclosed herein, e.g., as multicore imaging fiber 100 having a proximal tapered end 120, as multicore photonic crystal fibers 100 and/or as endoscope 150 with distal multicore fiber 100 optically coupled to jointedly-interconnected rigid image-relay elements 130.

FIG. 4D is a high level schematic illustration of temporal spectral multiplexing in illumination source 160, according to some embodiments of the invention. Illumination source 160 may comprise a fiber laser 162 comprising a broadband Bragg filter mirror 161 for a range of the specified plurality (N) of distinct wavelengths (denoted $\lambda_1$-$\lambda_N$), a controllable 1-to-N switch 164 connected to N narrowband Bragg filter mirrors 167 (denoted $\lambda_1 \ldots \lambda_N$), for the corresponding distinct wavelengths, each of narrowband Bragg filter mirrors 167 designed to reflect only the corresponding distinct wavelength. 1-to-N switch 164 may be controlled electrically (or mechanically, optically etc.). Illumination source 160 may further comprise a pumped gain in-fiber medium 163 connected between Bragg filter mirror 161 and controllable 1-to-N switch 164 with connected N narrowband Bragg filter mirrors 167. Illumination source 160 may further comprise multiplexer 165 (e.g., WDM) configured to combine illumination radiation from N narrowband Bragg filter mirrors 167 and provide illumination 65, delivered through illumination fiber 60 to tissue 90—simultaneously or in a temporally tunable manner with respect to the range or sub-ranges of the distinct wavelengths.

It is emphasized that the configuration illustrated in FIG. 4D may also be reversed to be used as spectrometer 170, as shown schematically in FIG. 4C with respect to FIG. 4B, for example, spectrometer 170 configured to provide narrow band imaging detection. In certain embodiments, narrow band imaging detection may be used for improved diagnosis of cancerous tissues.

Alternative or complementary implementations of spectral multiplexing may comprise a plurality of wavelength specific beam splitters or gratings, configured to provide the multiple narrowband spectral ranges at $\lambda_1 \ldots \lambda_N$.

Spectral multiplexing may be used to enhance any of various characteristics of fiber(s) 100 and endoscope(s) 150 such as resolution, field of view, working distance, depth of focus, 3D capability etc.—by multiplying the amount of information delivered through each core 110 by a factor of 10, 100 or even 1000 (depending on the spectral range and spectral resolution). These enhancements may be carries out with respect to one or more fiber modules in endoscope 150 and/or replace the need to use several fiber modules in the endoscope (fiber modules referring to associated fibers 100 which handle image delivery cooperatively). Spectral multiplexing may also be used to implement super resolved imaging achieved by various means, utilizing the multiple inputs per core 110 which correspond to the multiple wavelengths.

Wavelength Multiplexing Super Resolved Imaging

Figure 5A:
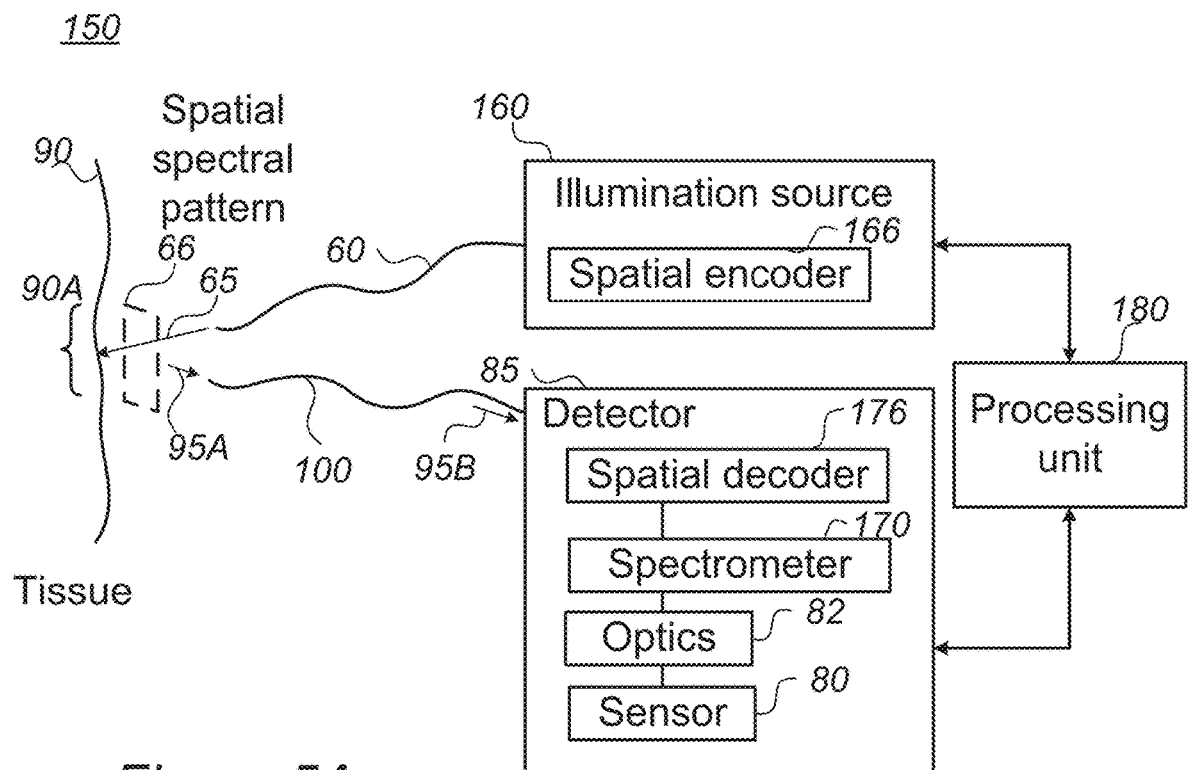
FIGS. 5A-5C are high level schematic illustrations of endoscopes and illumination sources thereof, configured to implement wavelength multiplexing super resolved imaging, according to some embodiments of the invention.
Figure 5B:
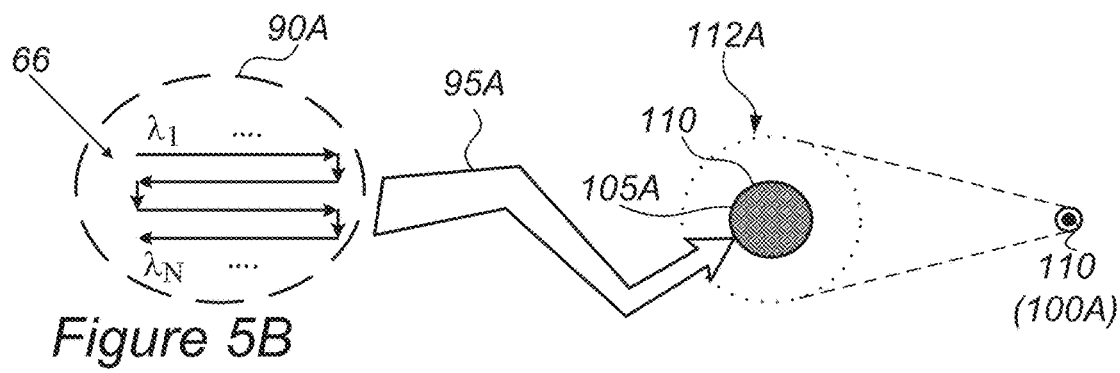
Figure 5C:
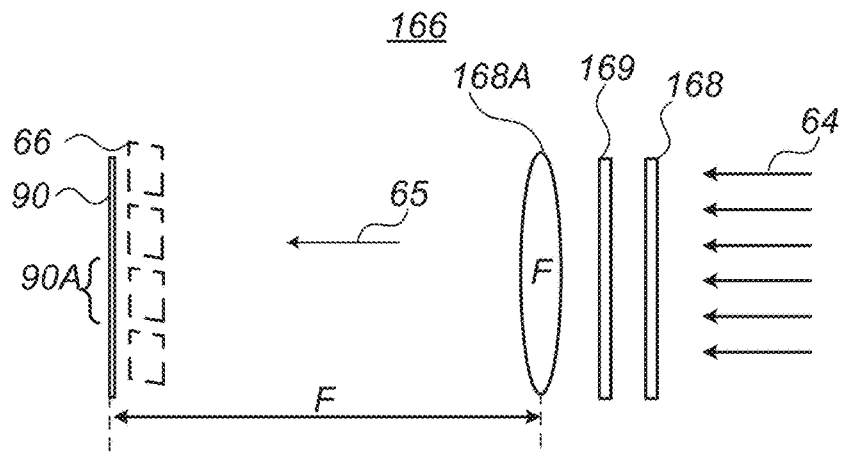

FIGS. 5A-5C are high level schematic illustrations of endoscope 150 and illumination sources 160 thereof, configured to implement wavelength multiplexing super resolved imaging, according to some embodiments of the invention. Endoscope 150 may be configured to have broadband illumination source 160, e.g., a white light source, and comprise a spatial encoder 166 configured to split the broadband illumination spatially, delivering different narrowband wavelength ranges to different locations on tissue 90 (illustrated schematically in FIG. 5A as pattern 66, FIG. 5B illustrates a non-limiting example for pattern 66). Spatial encoder 166 may comprise e.g., dispersive optical elements such as one or more gratings, transmissive optical elements such as one or more prisms and/or may possibly comprise de-multiplexer 175 as disclosed above for separating individual wavelengths $\lambda_1 \ldots \lambda_N$ from the broadband illumination in combination with elements such as DLP (digital light processing elements), mirror arrays etc.—and delivering different $\lambda_1 \ldots \lambda_N$ to different locations on tissue 90.

For example, the wavelength range $\lambda_1 \ldots \lambda_N$ may be scanned at a folded linear pattern 66 exemplified in FIG. 5B to cover given region 90A with different locations illuminated by different wavelengths $\lambda_1 \ldots \lambda_N$. The spatio-spectral resolution may be configured to cover larger region 90A with larger locations per wavelength, or smaller region 90A with smaller locations per wavelength; or alternatively or complementarily, the number of distinct wavelengths (N) and/or the wavelength range ($\lambda_1, \ldots \lambda_N$) may be configured to increase or reduce the spectrally-encoded spatial resolution.

Illumination 65 may therefore be configured to be spatially encoded by wavelength, illuminating each location on tissue 90 at a different wavelength, possibly according to a specified pattern 66. FIG. 5C illustrates schematically a non-limiting example for the optical implementation of illuminating pattern 66, namely by using a first grating 168 for implementing the spectral raster splitting and a second Dammann-like grating 169 configured to replicate the spectral raster encoding to fully illuminate the full field of view of tissue 90, illuminating pattern 66 on all tissue regions 90A of tissue 90 (illustrated in a highly schematic manner in FIG. 5C). Spatial encoder 166 may be configured to use white light illumination 64 with grating 168, 169 to deliver multiple illuminating patterns 66 to all tissue regions 90A of tissue 90, with radiation from each tissue region 90A delivered to a different core 110. Encoded radiation 65 may be delivered to tissue 90 through one or more optical element(s) 168A, e.g., configured to delivered focused encoded radiation 65, to project pattern 66 of tissue regions 90A (with the distance of optical element(s) 168A from tissue 90 being equal to the focus length, F, of optical element(s) 168A).

It is emphasized that fiber 100 may be configured to have sparse cores 110 (see FIGS. 1A, 1B), with some or each of cores 110 receiving radiation 105A from region 90A illuminated by full pattern 66 (or possibly a part thereof) so that the region between any two cores 110 may be multiplexed with wavelengths $\lambda_1 \ldots \lambda_N$ to make each spatial pixel guided in core 110 include actually many spatial points of information encoded by the different wavelengths according to pattern 66. The resulting is image, analyzed by spatial decoder 176, may therefore have much more spatial pixels of information than the number of cores 110 (e.g., maximally N times the number of cores).

Radiation 95A from tissue 90 may therefore be likewise spatio-spectrally encoded, and multicore fiber 100 may be configured to deliver radiation 95A from a region 90A (indicated schematically) of tissue 90, including multiple wavelengths which encode different locations in region 90A, to detector 85. Each core 110 may therefore be configured (e.g., by focusing and de-focusing) to deliver spectrally-encoded information from multiple locations on tissue 90, e.g., region 90A). Detector 85 may comprise spectrometer 170 (e.g., implemented as disclosed above, using principles disclosed in FIGS. 4C and/or 4D) and a spatial decoder 176 configured to decode spatial reflectivity information from the spectral information—providing N data points for each core 110. Therefore each core 110 may be used to deliver data for multiple pixels on sensor 80, which correspond to the spectrally encoded region 90A of tissue 90.

Certain embodiments comprise endoscope 150 comprising illumination source 160 comprising spatial encoder 166, configured to deliver illumination 65 at specified plurality of spatially-encoding distinct wavelengths $\lambda_1 \ldots \lambda_N$, with different wavelengths illuminating different locations on a tissue according to specified spatio-spectral pattern 66; detector 85 comprising spectrometer 170 and spatial decoder 176, configured to decode detected radiation 95B in specified plurality of distinct wavelengths $\lambda_1 \ldots \lambda_N$ according to specified spatio-spectral pattern 66; multicore imaging fiber 100 comprising cores 110 and configured to deliver (95B), through cores 110 to detector 85, image radiation 95A received from tissue 90 illuminated by illumination source 160, wherein at least some, or each core 110 is configured to deliver image radiation 95A from a tissue region illuminated by specified spatio-spectral pattern 66; and processing unit 180 configured to derive, from spatio-spectrally decoded detected image radiation 95B of single cores 110, image data corresponding to specified plurality of distinct wavelengths $\lambda_1 \ldots \lambda_N$ from image radiation delivered by each core 110. In certain embodiments, spatial encoder 166 may be implemented by first grating 168 configured to split broadband (e.g., white light) illumination into specified plurality of distinct wavelengths $\lambda_1 \ldots \lambda_N$ and second grating 169 configured to replicate the split broadband illumination to multiple patterns 66 corresponding to different regions of tissue 90.

Speckle Reduction

Figure 6:
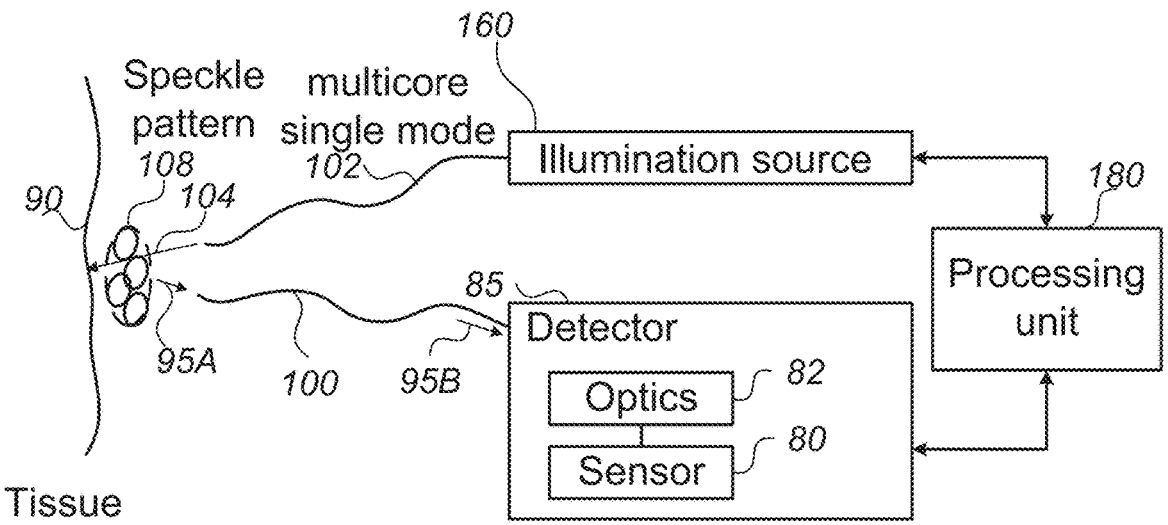
FIG. 6 is a high level schematic illustration of endoscopes with multimode, multicore illumination fibers, according to some embodiments of the invention.

FIG. 6 is a high level schematic illustration of endoscope 150 with a multimode, multicore illumination fiber 102, according to some embodiments of the invention. In certain embodiments, illumination source 160 may be configured to deliver illumination 104 through single mode, multicore illumination fiber 102 to generate a speckle pattern 108 on tissue 90 which is more uniform and with larger speckles than different types of illumination, such as by a multimode illumination fiber with a large-area core. Single mode, multicore illumination fiber 102 may be configured to have about the same area as a single core multimode illumination fiber, to deliver a comparable amount of illumination or energy, while delivering the illumination through multiple cores having almost identical axial lengths of the respective light channels (due to the fabrication process). As the optical paths are practically identical, resulting speckle pattern 108 consists of large speckles (due to interference of light coming from the different cores which are small in dimensions) and is more uniform than single core multimode illumination. Advantageously, larger speckles require simpler speckle averaging and reduction and are therefore advantageous with respect to resulting image quality and required processing power. Moreover, cores of single mode, multicore illumination fiber 102 may be optimized with respect to core size and number to maximize the size of speckles in the illumination channel and in pattern 108. Processing of the distal tip of illumination fiber 102 (e.g., may also be configured to enhance the coherence of illumination radiation delivered through different cores.

Processing unit 180 may be configured to identify and remove from delivered image radiation 95B, speckle pattern 108 from illumination 104 by single mode, multicore illumination fiber 102.

In certain embodiments, illumination may be implemented by one or more multimode multicore illumination fiber 102 with cores having a small number of multiple modes (e.g., 2-10 modes, or few tens, e.g., 10-30 modes) to provide additional flexibility in enhancing the uniformity of the speckle's formation altogether.

In certain embodiments, the shape of the illumination spot may be modulated to remove secondary speckle patterns, which depend on the spot size, by image processing. In certain embodiments, processing unit 180 may be configured to modulate, via illumination source 160, illumination 104 with respect to at least one illumination spot parameter such as any of the shape, the diameter and/or the spatial modes of the illumination spot, e.g., according to a specified pattern. Processing unit 180 may be further configured to use the specified pattern to analyze resulting changes in the image of the illumination spot, as detected by detector 85, and remove features of the image that fluctuate according to the specified pattern, as being related to secondary speckle patterns rather than to the imaged tissue. Advantageously, the contrast of the secondary speckle patterns may be significantly reduced and the image quality significantly improved. It is noted that removable secondary speckle patterns relate to features that may be modified by modulating illumination 104, while some residual, primary speckle patterns may remain, such as features relating e.g., to the size of the diffuser (not shown) through which illumination 104 is performed.

Hybrid Imaging Fiber

Figure 7A:
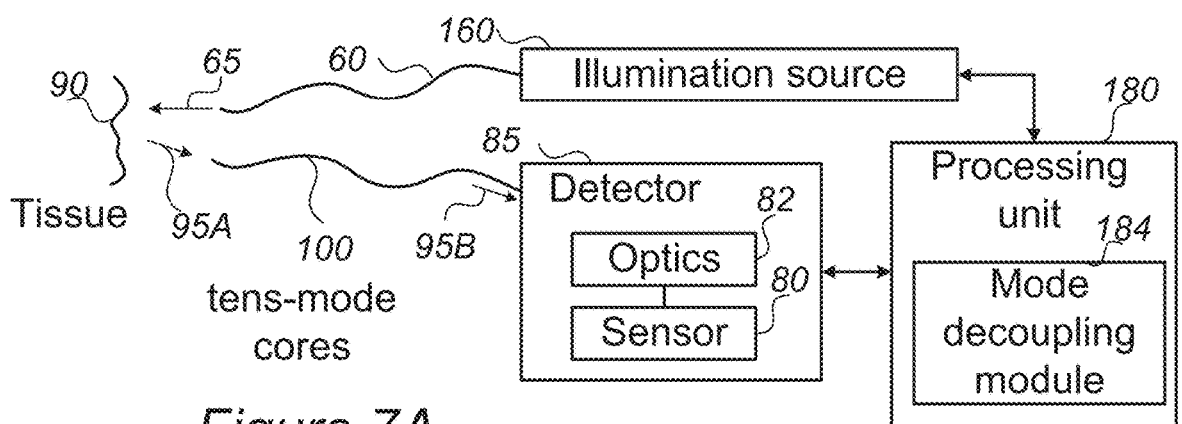
FIGS. 7A and 7B are high level schematic illustrations of endoscopes with multicore fibers with multimode cores having tens of modes, according to some embodiments of the invention.
Figure 7B:
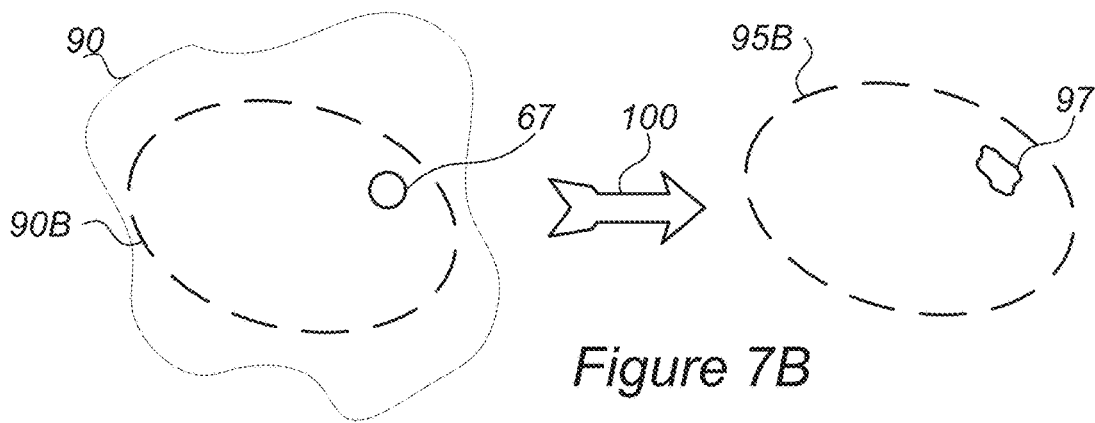

FIGS. 7A and 7B are high level schematic illustrations of endoscope 150 with multicore fiber 100 with multimode cores having tens of modes, according to some embodiments of the invention. Multicore fiber 100 may be configured to have a relatively small number of cores. e.g., several tens of modes (e.g., 10, 30, 50, 80) or a few hundred modes (e.g., 100, 150, 200) to implement a hybrid multicore fiber 100 in the sense that cores 110 are not single mode cores, but also not the customary multimode cores supporting many hundreds or thousands of modes. Complementarily, processing unit 180 may comprise a mode-decoupling module 184, configured to remove distortions which may be caused by mode mixing at bends of hybrid multicore fiber 100. Advantageously, while the use of multimode cores increases the information content of delivered radiation 95B, endoscope 150 does not become as sensitive to bending of fiber 100 as are prior art fibers supporting thousands or even tens of thousands of modes, because the computational effort in removing the distortions due to mode mixing is tolerable, and achievable by available processors for such applications.

When fiber 100 is bended in operation, the different modes are mixed and the image guided by through them is distorted, yet the distortions may be inverted by applying e.g., deep learning neural network algorithms by mode coupling module 184. Since every core 110 has small number of modes (e.g., tens of modes, much less than regular multimode fibers) the inversion of the modes-mixing due to bending may be carried out in real time.

In certain embodiments (see e.g., FIG. 7B as a non-limiting example), illumination source 160 may be configured to project a point (or any pattern) 67 on tissue 90 and processing unit 180 may be configured to estimate distortions by analyzing a distortion of illuminated point (or pattern) 67 in its image 97 (illustrated schematically) delivered through fiber 100 (within region 90B of tissue 90 imaged by fiber 100 and indicated schematically as image 95B). Mode coupling module 184 may be configured to enhance distortion cleaning calculations using the distortion estimation of illuminated point or pattern 67. Advantageously, the overall resolution is significantly increased without adding too much overload to the processing power of processing unit 180. For instance, in an illustrative non-limiting example, assuming a 450×450 micron fiber 100 with 20,000 cores 110, with every core 110 having 100 modes, the received image (95B) would have of 2M pixels instead of only 20K pixels when cores 110 are single mode. Certain embodiments of hybrid fiber 100 avoid both the difficulty in producing single mode cores in the multicore fiber and the requirement for rigidity in multimode fibers (to prevent mixing of modes which not feasible to correct) to combine the benefits of information increase when using multimode multicore fibers with reduced sensitivity to bending due to the relatively small number of modes.

Field of View Enhancing and Zooming

Figure 8A:
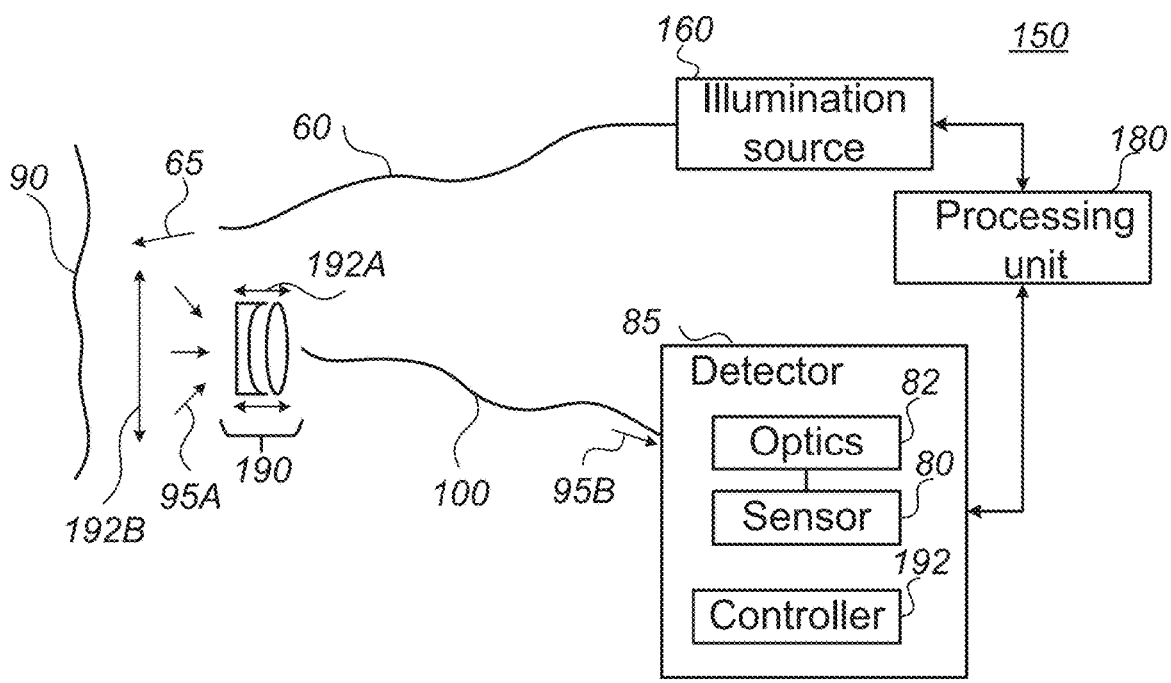
FIGS. 8A and 8B are high level schematic illustrations of endoscopes with enhanced field of view, according to some embodiments of the invention.
Figure 8B:
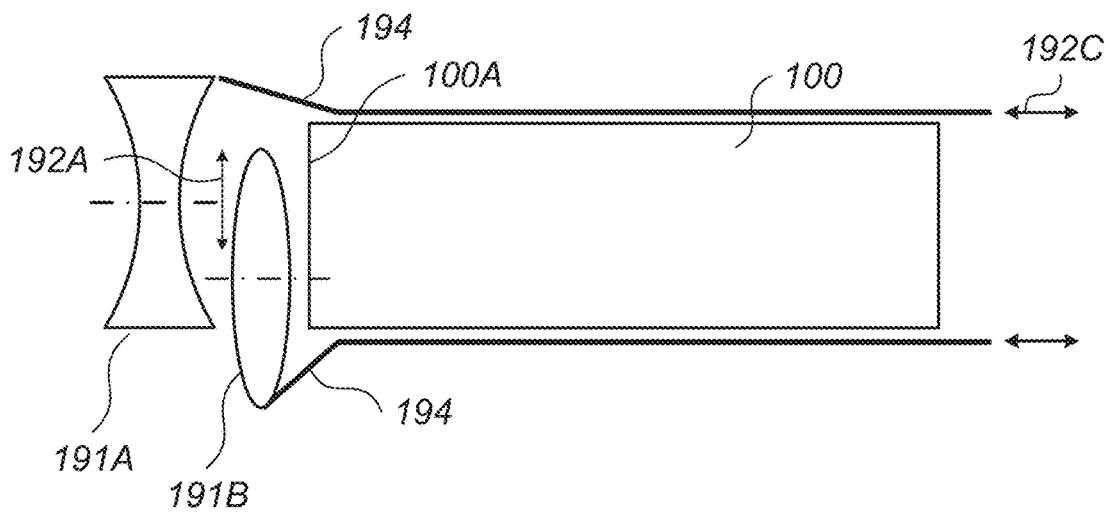

FIGS. 8A and 8B are high level schematic illustrations of endoscope 150 with enhanced field of view, according to some embodiments of the invention. In certain embodiments, endoscope 150 may be configured to have a large field of view without need to bend the distal tip of endoscope 150 and fiber 100. It is noted that the common practice of bending the distal tip of endoscope 150 to increase the field of view requires a large volume near tissue 90 for handling the distal tip of endoscope 150 (due to the limited bending radius thereof), while in disclosed embodiments a much smaller volume is required to accommodate disclosed distal tip optical elements 190 which provide a large enhancement of the field of view. Distal tip optical elements 190 may be configured to be controllably displaceable with respect to each other (perpendicularly to their optical axes), with relative displacement 192A configured to change the field of view (192B) of fiber 100, as illustrated schematically in FIG. 8A.

As illustrated schematically in FIG. 8B, in a non-limiting example, distal tip optical elements 190 may comprise a first lens 191A with a negative focal length and a second lens 191B with a positive focal length at distal tip 100A of fiber 100. Shifting 192A of the relative position of lenses 191A. 191B may be configured to implement a tunable prism (see Equation 1 below). With distal tip optical elements 190, shifting (192A) lenses 191A. 191B with respect to each other increases the field of view (192B) of endoscope 150 by increasing only the size of the distal tip of endoscope 150 without requiring to bend the distal tip of endoscope 150, which requires large free volume available. Moreover, changing the distance (192A) between lenses 191A. 191B may be configured to realize optical zooming (alternatively or possibly in addition to field of view enhancement). A mechanism 194 may be configured to perform shifts 192A between lenses 191A, 191B (perpendicularly to their optical axes). For example, mechanical implementations of mechanism 194 may comprise controllably movable sleeves connected to lenses 191A, 191B and/or by springs similar to existing springs connected to the navigation shield (not shown) of endoscope 150 which may transfer a longitudinal shift 192C of these elements to perpendicular shift 192A of lenses 191A, 191B.

The following Equation 1 demonstrates that changing a relative shift between lenses 191A, 191B (left-hand expression in Equation 1) is equivalent to a prism (right-hand expression in Equation 1) with an angle that is proportional to the amount of the relative shift (192A) between lenses 191A, 191B, with T(x) denoting the overall transmission expression of lenses 191A. 191B as illustrated schematically in FIG. 8B, having the same focal length F in absolute value (lens 191A with −F and 191B with +F), positioned sequentially with a relative transversal shift of 2Δx between them, and λ denoting the optical wavelength.

$$T(x) = \exp\left(-\pi i \frac{(x-\Delta x)^2}{\lambda F}\right) \exp\left(\pi i \frac{(x+\Delta x)^2}{\lambda F}\right) = \exp\left(\frac{4\pi i \Delta x x}{\lambda F}\right) \quad \text{Equation 1}$$

The overall transmission expression of the emulated prism (right-hand expression in Equation 1) reflects a prism positioned on the aperture plane of an imaging lens which shifts the obtained image by a factor of 2Δx which is exactly the relative shift between two lenses 191A. 191B. By tuning (192A) the amount of shift (by changing Δx), the field of view of fiber 100 may be scanned, providing a larger field of view than merely the physical field of view of the given imaging lens.

Longitudinally-Sensing Endoscope

FIGS. 9A-9C are high level schematic illustrations of longitudinally-sensing endoscope 150, according to some embodiments of the invention. In certain embodiments, endoscope 150 may be configured to have sensing capabilities along at least part of its length. For example, fiber 100 may be configured to have a plurality of peripheral radiation entrance locations 195 ("windows"), configured to allow radiation from the sides of fiber 100 to enter peripheral cores 110C of fiber 100, as illustrated schematically in FIGS. 9A-9C. Different peripheral cores 110C may be configured along fiber 100 to receive radiation 95C from different locations, e.g., from locations along a body conduit 91 such as a blood vessel, by corresponding configuration of peripheral radiation entrance locations 195 along endoscope 150. Illumination fiber 60 may be configured to emit radiation 65A along endoscope 150, to improve or enable sensing reflected radiation 95C from surrounding tissue 91 by fiber 100.

For example, peripheral radiation entrance locations 195 may be arranged in circles 195, each circle 195 being connected to a different peripheral core 110C as illustrated schematically in FIG. 9B. Such configurations may be used to extract the distance of fiber 100 from tissue 91 along its longitudinal axis by extracting the readout of peripheral cores 110C while internal cores 110 are used to imaging explained above. The longitudinal sensing may therefore be used to improve the control of endoscope 150, avoiding lateral damage to tissue 91 and provide data concerning tissue 91. In certain embodiments, peripheral radiation entrance locations 195 such as circles 195 may be formed by controlled twisting of the pre-form during its drawing to yield fiber 100. FIG. 9C provides a non-limiting example for such actual fiber 100 with slits 195 produced by the inventors.

Endoscope 150 may further comprise processing unit 180 configured to derive longitudinal data 198 from radiation 95C delivered through the specified peripheral cores, in addition to image data 197 delivered from the distal tip of fiber 100. Illumination fiber 60 may correspondingly be configured to emit radiation 65A along endoscope 150, in addition to illuminating 65 tissue 90 at the distal end thereof. Endoscope 150 may be further configured, e.g., via processing unit 180, to derive indications for tissue 91 in proximity to fiber 100 along its length.

Wave-Front Sensing

Figure 10:
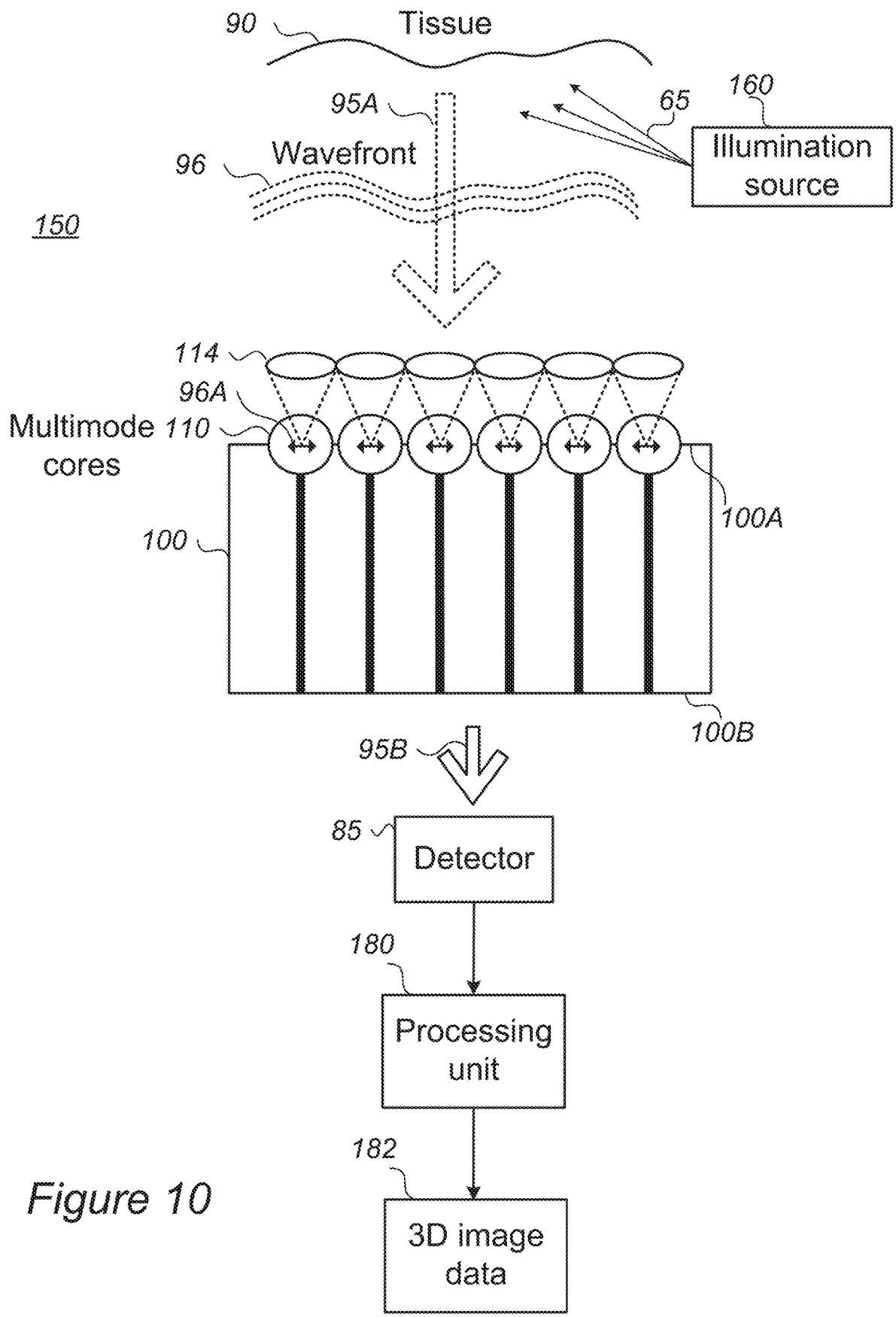
FIG. 10 is a high level schematic illustration wave-front sensing endoscopes, according to some embodiments of the invention.

FIG. 10 is a high level schematic illustration wave-front sensing endoscopes 150, according to some embodiments of the invention.

Endoscope 150 may comprise illumination source 160, configured to deliver illumination 65 at a specified plurality of spatially distinct locations on tissue 90, detector 85 and multicore imaging fiber 100 comprising multimode cores 110 which are configured to support more than one radiation mode in core 110, e.g., any of 2-6 modes, or possibly between 2-10 or 2-20 modes (configured, without being bound by theory, according to $V=\pi \cdot A \cdot (NA/\lambda)^2$, with V the number of modes, A the cross sectional area of core 110. NA the numerical aperture of core 110 and λ the corresponding wavelength, see the detailed analysis below). Multicore imaging fiber 100 may be configured to deliver, through multimode cores 110 to detector 85, wave-front radiation 96 received from tissue 90 illuminated by illumination source 180. Wave-front radiation 96 may be delivered though cores 110 without any optical elements at distal fiber tip 100A, or as modified wave-front radiation 96A which may be modified by optical elements 114 between distal fiber tip 100A and tissue 90 (e.g., perforations, lenslets, Shack Hartmann interferometer configurations, pinholes array configurations, etc.). For example, optical elements 114 may be configured to focus sections of wave-front radiation % into cores 110, to generate modified wave-front radiation % A in which phase information in wave-front radiation % is modified to spatial information (e.g., orthogonal focus point translations illustrated schematically by the double-headed arrow), which is delivered through cores 110 along multicore fiber 100. Endoscope 150 may further comprise processing unit 180 configured to derive, from the delivered wave-front radiation % and/or % A, three dimensional (3D) image data 182 derived from wave-front radiation %, e.g., according to spot position changes associated with each or some of cores 110. The spot position changes indicate the angle of the wave-front entering respective cores 110.

An example for such configurations follows. The number of modes supported by multimode cores 110 may be selected as a tradeoff between information delivery capacity of cores 110 and the sensitivity of the delivered modes to bending of fiber 100 (e.g., configurations less prone to bending, cores 110 may be configured to support more modes). This tradeoff is described below, and fibers 100 may be configured to implement various tradeoffs, with cores supporting a range of number of modes. The number of modes (V) may be expressed by Equation 2, with NA denoting the numerical aperture, a is the radius of a core, λ denoting the wavelength of the light, and $n_{core}$ and $n_{cladding}$ denoting the corresponding refractive indices.

$$V = \frac{2\pi a}{\lambda} NA = \frac{2\pi a}{\lambda} \sqrt{n_{core}^2 - n_{cladding}^2} \quad \text{Equation 2}$$

The single mode condition requires V<2.405 and the number of modes (M) is proportional to $2 \cdot (V/2.405)^2$, or specifically for a step index fibers $M=4V^2/\pi^2$. The tradeoff of the number of modes with respect to crosstalk between cores 110 may be expressed in terms of the width of the Gaussian profile of the field propagating through optical core 110 (denoted by W, defined for a field value that is 1/e of its maximal value) and the pitch L between cores 110—expressed in Equations 3 in terms of V (number of modes) and a (core radius). For example, a condition for preventing crosstalk between cores 110 may be defined as L≥2W, providing a relation between pitch (L) and core radius (a).

$$W = a\left(0.65 + \frac{1.619}{V^{1.5}} + \frac{2.879}{V^6}\right); L = 2a\left(0.65 + \frac{1.619}{V^{1.5}} + \frac{2.879}{V^6}\right) \quad \text{Equation 3}$$

Such condition may be balanced in fiber design with respect to the 3D resolution achievable by the core multimode configuration, which may be expressed as follows. The 3D resolution in space equals to the pitch size L (related to the core size) and the resolution in phase #sensitivity to wavefront 96 equals to $2\pi/\sqrt{M}$ in every axis (y and x). Thus, the angular sensitivity in the direction of propagation along the axial direction Z, $\Delta\theta_z$, may be expressed and approximated and expressed in to Equation 4.

$$\Delta\theta_z \approx \frac{\pi\lambda}{4a\left(0.65V + \frac{1.619}{V^{0.5}} + \frac{2.879}{V^5}\right)} \approx \frac{1.21\lambda}{aV} = 0.2\frac{\lambda^2}{NAa^2} \quad \text{Equation 4}$$

The reciprocal relation between $\Delta\theta_z$ and V indicates that increasing the number of modes (V) improves sensitivity (as smaller angles $\Delta\theta$ can be sensed) but as shown above, increasing V also increases the sensitivity to fiber bending (increases crosstalk through modes coupling). The reduction in the bending angle (affects the bending radius of the fiber) is proportional to the root of the number of modes, $\sqrt{M}$, which is proportional to $4a \cdot NA/\lambda$.

Equations 2-4 and the considerations presented above clearly describe the ways specific fiber configurations may be carried out to optimize endoscope performance with respect to mechanical requirements and wave-front sensing (3D resolution) requirements. Various applications of endoscope may imply different fiber configurations with respect to fiber rigidness, core parameters (size and pitch) and achieved spatial resolution.

It is noted that wave-front sensing endoscopes 150 may be implemented as any of the embodiments disclosed herein, e.g., as multicore imaging fiber 100 having a proximal tapered end 120, as multicore photonic crystal fibers 100 and/or as endoscope 150 with distal multicore fiber 100 optically coupled to jointedly-interconnected rigid image-relay elements 130.

Figure 11:
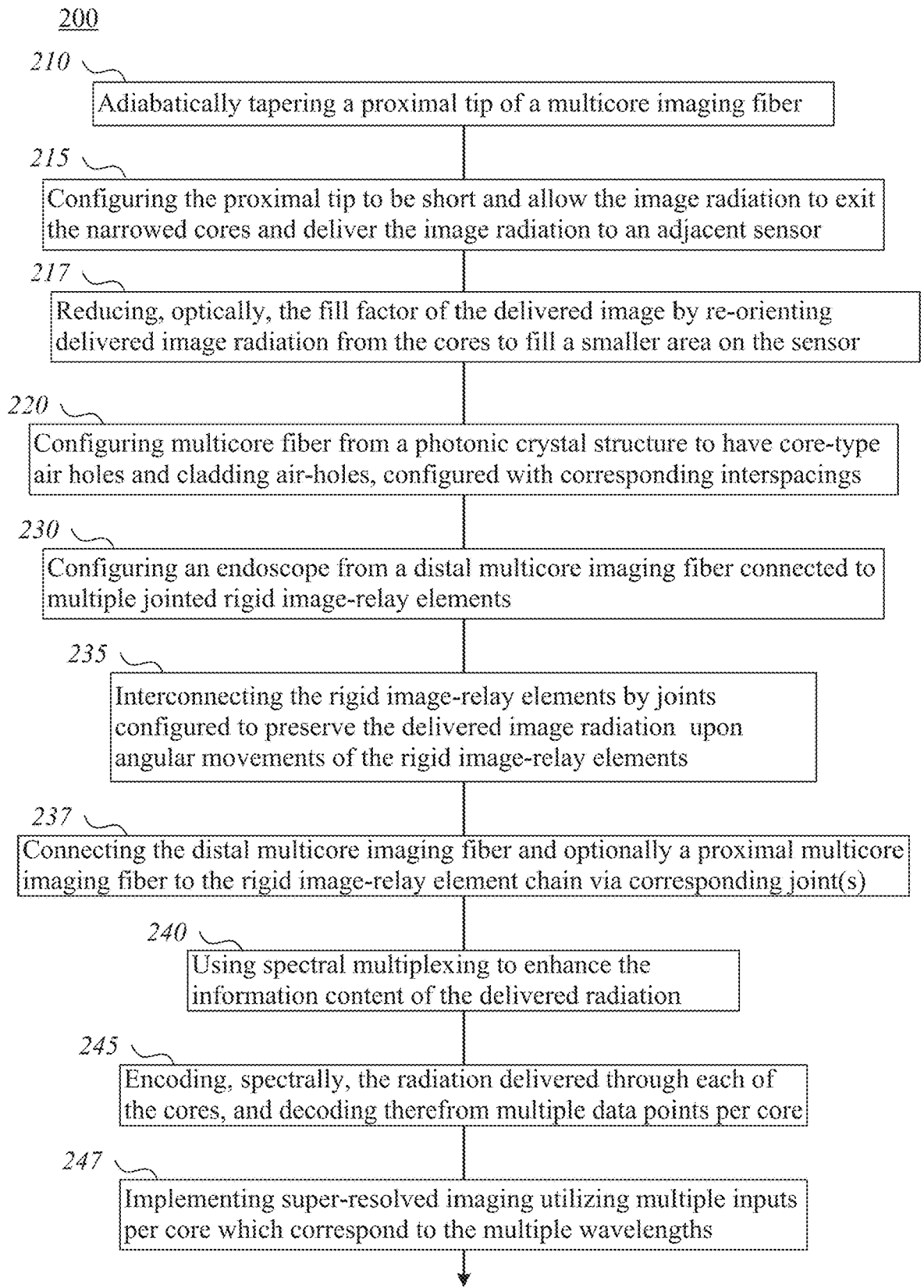
FIG. 11 is a high level flowchart illustrating a method, according to some embodiments of the invention.
Figure 11:
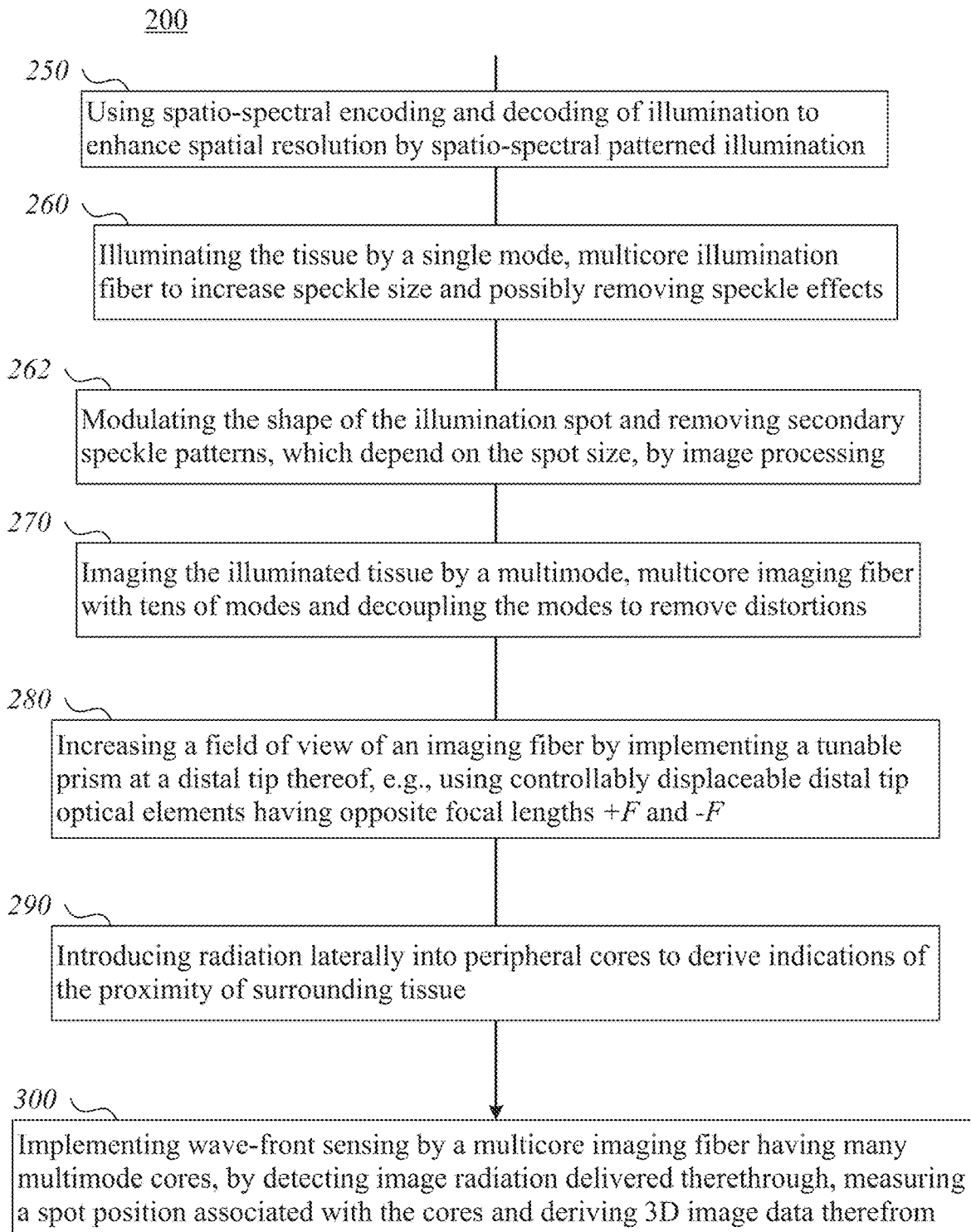

FIG. 11 is a high level flowchart illustrating a method 200, according to some embodiments of the invention. The method stages may be carried out with respect to endoscopes 150 and/or fibers 100 described above, which may optionally be configured to implement method 200. Method 200 may be at least partially implemented by at least one computer processor. Certain embodiments comprise computer program products comprising a computer readable storage medium having computer readable program embodied therewith and configured to carry out of the relevant stages of method 200. Method 200 may comprise stages for producing, preparing and/or using device endoscopes 150 and/or fibers 100, such as any of the following stages, irrespective of their order.

Method 200 may comprise adiabatically tapering a proximal tip of a multicore imaging fiber (stage 210) comprising at least 10,000 cores with a common cladding, configured to deliver image radiation from tissue at a distal end of the fiber, wherein the image radiation is confined within the cores and the cores are interspaced within a fiber cross-sectional area to prevent cross-talk therebetween, and configuring the adiabatically tapered proximal tip (stage 215) to be shorter than 1cm and have a fiber cross-sectional area and a core diameter which are reduced by a factor of at least 3 with respect to the multicore imaging fiber, to allow the image radiation exit the narrowed cores and deliver the image radiation to an adjacent sensor. Certain embodiments comprise reducing, optically, the fill factor of the delivered image by re-orienting delivered image radiation from the cores to fill a smaller area on the sensor (stage 217).

Method 200 may comprise configuring multicore fiber from a photonic crystal structure (stage 220) composed of multiple air holes, by designing the air holes to be in at least two types: core-type air holes, interspaced within a fiber cross-sectional area at a specified core-pitch selected to confine image radiation within the core-type air holes, and cladding air-holes between the core-type air holes, the cladding air-holes interspaced within the fiber cross-sectional area at a specified cladding-pitch selected to prevent cross-talk between the core-type air holes.

Method 200 may comprise configuring an endoscope from a distal multicore imaging fiber and a plurality of rigid image-relay elements (stage 230), wherein the distal multicore imaging fiber is configured to receive image radiation from tissue at a proximal end thereof and deliver the image radiation to a distal end of the distal multicore imaging fiber, and interconnecting the rigid image-relay elements by a respective plurality of joints (stage 235), wherein a distal one of the rigid image-relay elements is connected via a corresponding joint to the proximal end of the distal multicore imaging fiber. The joints are configured to preserve the delivered image radiation from the proximal end of the distal multicore imaging fiber upon angular movements of the rigid image-relay elements with respect to each other, to deliver the image radiation at a proximal end of the endoscope.

Method 200 may further comprise connecting a proximal multicore imaging fiber (stage 237) to a proximal one of the rigid image-relay elements via a corresponding joint, to deliver the image radiation from the proximal rigid image-relay element.

Method 200 may comprise using spectral multiplexing to enhance the information content of the delivered radiation (stage 240) and encoding, spectrally, the radiation delivered through each of the cores, and decoding therefrom multiple data points per core (stage 245). For example, method 200 may comprise illuminating tissue by a specified plurality of distinct wavelengths, delivering image radiation received from illuminated tissue through each of a plurality of cores of a multicore imaging fiber, decoding, for each of the cores, detected radiation in the specified plurality of distinct wavelengths, and deriving from the decoded detected image radiation of each of the cores, image data corresponding to the specified plurality of distinct wavelengths. Method 200 may further comprise implementing super resolved imaging utilizing multiple inputs per core which correspond to the multiple wavelengths (stage 247).

Method 200 may comprise using spatio-spectral encoding and decoding of illumination to enhance spatial resolution by spatio-spectral patterned illumination (stage 250), e.g., by illuminating tissue by a specified plurality of distinct wavelengths at a specified spatio-spectral pattern, delivering image radiation received from illuminated tissue through each of a plurality of cores of a multicore imaging fiber, decoding, for each of the cores, detected radiation in the specified plurality of distinct wavelengths according to the specified spatio-spectral pattern, and deriving from the decoded detected image radiation of each of the cores, image data corresponding to the specified plurality of distinct wavelengths and according to the specified spatio-spectral pattern.

Method 200 may comprise illuminating the tissue by a single mode, multicore illumination fiber to increase speckle size and possibly removing speckle effects (stage 260), e.g., by using a single mode, multicore illumination fiber to illuminate a tissue imaged by a multicore imaging fiber and optionally identifying and removing from image radiation delivered by a multicore imaging fiber, a speckle pattern from the illumination by the single mode, multicore illumination fiber. Method 200 may further comprise modulating the shape of the illumination spot and removing secondary speckle patterns, which depend on the spot size, by image processing (stage 262).

Method 200 may comprise imaging an illuminated tissue by a multicore imaging fiber having cores configured to support between 10-100 modes, and decoupling the modes by removing mode-mixing distortions from image radiation delivered by the fiber (stage 270).

Method 200 may comprise increasing a field of view of an imaging fiber (stage 280) by implementing a tunable prism at a distal tip thereof. e.g., by controllably displacing distal tip optical elements with respect to each other to change a field of view of the fiber, possibly using distal tip optical elements with opposite focal lengths +F and −F.

Method 200 may comprise introducing radiation laterally into peripheral cores to derive indications of the proximity of surrounding tissue (stage 290), e.g., by enabling radiation to enter through sides of a multicore imaging fiber and into specified peripheral cores thereof, and deriving longitudinal data concerning tissue surrounding the fiber from radiation delivered through the specified peripheral cores. For example, method 200 may comprise designing peripheral slits in the fiber to enable the radiation enter the specified peripheral cores.

Method 200 may comprise implementing wave-front sensing by a multicore imaging fiber having at least 10,000 multimode cores, by detecting image radiation delivered therethrough, measuring a spot position associated with the cores and deriving 3D image data therefrom (stage 300).

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method comprising using a single mode, multicore illumination fiber to illuminate a tissue imaged by a multicore imaging fiber, the method further comprising identifying and removing from image radiation delivered by a multicore imaging fiber, a speckle pattern from the illumination by the single mode or multimode, multicore illumination fiber.

2. The method of claim 1, wherein the identifying and removing are carried out by modulating a shape of the illumination spot and removing secondary speckle patterns by image processing.

3. An endoscope comprising:
   an illumination source, configured to deliver illumination at a specified plurality of distinct wavelengths,
   a detector comprising a spectrometer configured to decode detected radiation in the specified plurality of distinct wavelengths,
   a multicore imaging fiber comprising a plurality of cores and configured to deliver, through the cores to the detector, image radiation received from tissue illuminated by the illumination source, and
   a processing unit configured to derive, from the decoded detected image radiation of each of the cores, image data corresponding to the specified plurality of distinct wavelengths,
   wherein the illumination source comprises:
      a fiber laser comprising:
      a broadband Bragg filter mirror for a range of the specified plurality (N) of distinct wavelengths,
      a controllable 1-to-N switch connected to N narrowband Bragg filter mirrors for the corresponding distinct wavelengths, each of narrowband Bragg filter mirrors designed to reflect only the corresponding distinct wavelength, and
      a pumped gain in-fiber medium connected between the Bragg filter mirror and the controllable 1-to-N switch with the connected N narrowband Bragg filter mirrors; and
      a wavelength-division multiplexer (WDM) configured to combine illumination radiation from the N narrowband Bragg filter mirrors.

4. An endoscope comprising:
   an illumination source, configured to deliver illumination at a specified plurality of distinct wavelengths,
   a detector comprising a spectrometer configured to decode detected radiation in the specified plurality of distinct wavelengths,
   a multicore imaging fiber comprising a plurality of cores and configured to deliver, through the cores to the detector, image radiation received from tissue illuminated by the illumination source, and
   a processing unit configured to derive, from the decoded detected image radiation of each of the cores, image data corresponding to the specified plurality of distinct wavelengths, the endo scope further configured to utilize the multiple distinct wavelengths to implement a spectrometer for narrow band imaging detection.

5. An endoscope comprising a single mode, multicore illumination fiber and a multicore imaging fiber, the multicore imaging fiber configured to deliver image radiation from a tissue illuminated by the single mode, multicore illumination fiber, wherein the endoscope further comprises a processing unit configured to identify and remove from the delivered image radiation, a speckle pattern from the illumination by the single mode, multicore illumination fiber.

6. The endoscope of claim 5, wherein the processing unit is further configured to modulate the illumination with respect to at least one illumination spot parameter according to a specified pattern, and to use the specified pattern to analyze resulting changes in the delivered image radiation and remove features of the delivered image radiation that fluctuate according to the specified pattern, as being related to secondary speckle patterns.

7. An endoscope comprising:
an illumination source comprising a spatial encoder, configured to deliver illumination at a specified plurality of spatially-encoding distinct wavelengths, with different wavelengths illuminating different locations on a tissue according to a specified spatio-spectral pattern,
a detector comprising a spectrometer and a spatial decoder, configured to decode detected radiation in the specified plurality of distinct wavelengths according to the specified spatio-spectral pattern,
a multicore imaging fiber comprising a plurality of cores and configured to deliver, through the cores to the detector, image radiation received from tissue illuminated by the illumination source, wherein each core is configured to deliver image radiation from a tissue region illuminated by the specified spatio-spectral pattern, and
a processing unit configured to derive, from the spatio-spectrally decoded detected image radiation of each of the cores, image data corresponding to the specified plurality of distinct wavelengths from image radiation delivered by each core.

8. The endo scope of claim 7, wherein the spatial encoder is implemented by a first grating configured to split broadband illumination into the specified plurality of distinct wavelengths and a second grating configured to replicate the split broadband illumination to multiple patterns corresponding to different regions of the tissue.

9. A method comprising:
illuminating tissue by a specified plurality of distinct wavelengths at a specified spatio-spectral pattern,
delivering image radiation received from illuminated tissue through each of a plurality of cores of a multicore imaging fiber,
decoding, for each of the cores, detected radiation in the specified plurality of distinct wavelengths according to the specified spatio-spectral pattern, and
deriving from the decoded detected image radiation of each of the cores, image data corresponding to the specified plurality of distinct wavelengths and according to the specified spatio-spectral pattern.

* * * * *